US010059952B2

(12) United States Patent
Nett

(10) Patent No.: US 10,059,952 B2
(45) Date of Patent: *Aug. 28, 2018

(54) YEAST STRAINS FOR PROTEIN PRODUCTION

(71) Applicant: GLYCOFI, INC., Lebanon, NH (US)

(72) Inventor: Juergen Nett, Grantham, NH (US)

(73) Assignee: GLYCOFI, INC., Lebanon, NH (US)

( * ) Notice: Subject to any disclaimer, the term of this patent is extended or adjusted under 35 U.S.C. 154(b) by 331 days.

This patent is subject to a terminal disclaimer.

(21) Appl. No.: 14/836,203

(22) Filed: Aug. 26, 2015

(65) Prior Publication Data

US 2015/0361438 A1    Dec. 17, 2015

Related U.S. Application Data

(63) Continuation of application No. 12/744,959, filed as application No. PCT/US2008/013719 on Dec. 15, 2008, now Pat. No. 9,133,464.

(60) Provisional application No. 61/008,242, filed on Dec. 19, 2007.

(51) Int. Cl.
*C12N 15/81* (2006.01)
*C12N 9/88* (2006.01)

(52) U.S. Cl.
CPC ............ *C12N 15/815* (2013.01); *C12N 9/88* (2013.01); *C12N 2800/102* (2013.01); *C12Y 401/01021* (2013.01)

(58) Field of Classification Search
None
See application file for complete search history.

(56) References Cited

U.S. PATENT DOCUMENTS

| | | | |
|---|---|---|---|
| 5,584,039 A | 12/1996 | Johnson et al. | |
| 6,312,690 B1 * | 11/2001 | Edelman | C07K 16/34 424/133.1 |
| 7,029,872 B2 | 4/2006 | Gerngross | |
| 7,319,009 B2 * | 1/2008 | Klein | C07K 14/723 435/254.2 |
| 7,479,389 B2 | 1/2009 | Nett et al. | |
| 2004/0018590 A1 | 1/2004 | Gerngross et al. | |
| 2004/0229306 A1 | 11/2004 | Nett | |
| 2005/0026598 A1 | 2/2005 | Patel et al. | |
| 2005/0118648 A1 | 6/2005 | Li | |
| 2006/0040353 A1 | 2/2006 | Davidson et al. | |
| 2006/0252096 A1 | 11/2006 | Zha et al. | |
| 2007/0072262 A1 | 3/2007 | Nett et al. | |
| 2007/0118916 A1 | 5/2007 | Puzio et al. | |
| 2007/0202569 A1 | 8/2007 | Miura et al. | |
| 2008/0139470 A1 | 6/2008 | Sethuraman et al. | |
| 2009/0124000 A1 | 5/2009 | Nett et al. | |
| 2010/0279348 A1 | 11/2010 | Nett | |

FOREIGN PATENT DOCUMENTS

| | | |
|---|---|---|
| EP | 1283265 A1 | 12/2003 |
| EP | 1918379 | 5/2008 |
| EP | 1283265 B1 | 5/2009 |
| WO | 199859037 | 12/1998 |
| WO | 200190393 | 11/2001 |
| WO | 2004072280 | 8/2004 |
| WO | 200524015 | 3/2005 |
| WO | 2005042750 | 5/2005 |
| WO | 2007136695 | 11/2007 |
| WO | 200852797 | 5/2008 |

OTHER PUBLICATIONS

Gedvilaite et al. (Control of the expression of the ADE2 gene of the yeast *Saccharomyces cerevisiae*, Curr Genet (1994)25:475-479).*
PichiaPinkr™ Expression System, User Guide, Life Technologies, 2014.
Ogunjimi, "High-level secretory expression of immunologically active . . . ", Biotech Letters (1999), vol. 21, pp. 561-567.
Vervecken, "In vivo synthesis of mammalian-like, hybrid-type N-glycans . . . ", App. & Environ. Microbiol. (2004), vol. 70, pp. 2639-2646.
Jones, "Regulation of amino acid and nucleotide biosynthesis . . . ", The Molecular Biology of the Yeast *Saccharomyces*: Metabolism and Gene Expression (Cold Spring Harbor Laboratory Press, Cold Spring Harbor, NY, 1982), pp. 181-299.
Higgins, "Small vectors of expression based on dominant drug resistance . . . ", Methods in Molecular Biology (1998), vol. 103, pp. 41-53.
Bobrowicz, "Engineering of an artificial glycosylation pathway . . . ", Glycobiology (2004), vol. 14, pp. 757-766.
Lin Cereghino, "Production of recombinant proteins in fermenter . . . ", Current Opin. in Biotech (2002), vol. 13, pp. 329-332.
Choi, "Use of combinatorial genetic libraries . . . ", PNAS (2003), vol. 100, pp. 5022-5027.
Hamilton, "Humanization of yeast to produce complex terminally . . . ", Science (2006), vol. 313, pp. 1441-1443.
Hamilton, "Integrative transformation of Candida albicans, . . . ", Molecular and Cellular Biol. (1986), vol. 6, pp. 142-149.
Kurtz, "Integrative transformation of Candida albicans, . . . ", Molecular and Cellular Biol. (1986), vol. 6, pp. 142-149.
Jin, "Adenine auxotrophic mutants of Aspergilus oryzae: . . . ", Biosci. Biotech. Biochem. (2004), vol. 68, pp. 656-662.
Lin Cereghino, "New selectable marker/auxotrophic host strain . . . ", Gene (2001), vol. 263, pp. 159-169.
Myasnikov, "The *Saccharomyces cerevisiae* ADE1 gene: . . . ", Gene (1991), vol. 109, pp. 143-147.

(Continued)

*Primary Examiner* — Suzanne Marie Noakes
*Assistant Examiner* — Jae W Lee
(74) *Attorney, Agent, or Firm* — John David Reilly; Laura Ginkel

(57) ABSTRACT

Method and system for expression systems, based on ade1 and ade2 auxotrophic strains of yeast and fungi, including *P. pastoris* are disclosed. The expression systems are useful for increased cellular productivity of transformed cell lines and for production of recombinant glycoproteins at industrial scale.

9 Claims, 9 Drawing Sheets

Specification includes a Sequence Listing.

(56) References Cited

OTHER PUBLICATIONS

Nett, "Cloning and disruption of the Pichia pastoris ARG1, . . . ", Yeast (2005), vol. 22, pp. 295-304.
Nett, "Cloning and disruption of the PpURA5 gene . . . ", Yeast (2003), vol. 20, pp. 1279-1290.
Piontek, "Two novel gene expression systems based on the yeasts . . . ", Appl. Microbiol. Biotech. (1998), vol. 50, pp. 331-338.
Zonneveld, "The red ade mutants of Kluyveromyces Lactis . . . ", Yeast (1995), vol. 11, pp. 823-827.

* cited by examiner

```
S. cerevisiae ADE2  MDSRTVGILGGGQLGRMIVEAANRLNIKTVILDAENSPAKQISNSNDHVN   50
P. pastoris ADE2    MDSQVIGILGGGQLGRMIVEAASRLNIKTVILDDGFSPAKHINAAQDHID   50

S. cerevisiae ADE2  GSFSNPLDIEKLAEKCDVLTIEIEHVDVPTLKNLQVKHPKLKIYPSPETI  100
P. pastoris ADE2    GSFKDEEAIAKLAKCDVLTVEIEHVNTDALKRVQDRTG-IKIYPLPETI   99

S. cerevisiae ADE2  RLIQDKYIQKEHLIKNGIAVTQSVPVEQASETSLLNVGRDLGFPFVLKSR  150
P. pastoris ADE2    RLIKDKYLQKEHLIKHHISVTKSQGIE-SNEKALLLFGEENGFPYLLKSR  148

S. cerevisiae ADE2  TLAYDGRGNFVVKNKEMIPEALEVLKDRPLYAEKWAPFTKELAVMIVRSV  200
P. pastoris ADE2    TMAYDGRGNFVVESKEDISKALEFLKDRPLYAEKFAPFVKELAVMVVRSL  198

S. cerevisiae ADE2  NGLVFSYPIVETIHKDNICDLCYAPARVPDSVQLKAKLLAENAIKSFPGC  250
P. pastoris ADE2    EGEVFSYPTIVETIVHKDNICHIVYAPARVNDTIQKKAQILAENTVKTFPGA  248

S. cerevisiae ADE2  GIFGVEMFYLETGELLINEIAPRPHNSGHYTIDACVTSQFEAHLRSILDL  300
P. pastoris ADE2    GIFGVEMFLLSDGELLVNEIAPRPHNSGHYTIDACVTSQFEAHVRAITGL  298

S. cerevisiae ADE2  PMPKNFTSFSTITTNAIMLNVLGDKHTKDKELETCERALATPGISVYLYG  350
P. pastoris ADE2    PMPLDFTKLSTSNTNAIMLNVLGAEKSHG-ELEFCRRALETPGASVYLYG  347

S. cerevisiae ADE2  KESRPNRKVGHINITIASSMAECEQRLNYITGRTDIPIKISVAQKLDLEAM  400
P. pastoris ADE2    KTTRLARKMGHINILIGSSMLEAEQKLEYILEESTHLPSSTVS---AD   391

S. cerevisiae ADE2  VKPLVGIIMGSDSDLPVMSAACAVLKDFGVPFEVTIVSAHRTPHRMSAYA  450
P. pastoris ADE2    TKPLVGVIMGSDSDLPVIISKGCDILKQFGVPFEVTIVSAHRTPQRMTRYA  441

S. cerevisiae ADE2  ISASKRGIKITIIAGAGGAAHLPGMVAAMTPLPVIGVPPVKGSCLDGVDSLH  500
P. pastoris ADE2    FEAASRGIKALIAGAGGAAHLPGMVAAMTPLPVIGVPPVKGSTLDGVDSLH  491

S. cerevisiae ADE2  SIVQMPRGVPVATVAINNSTNAALLAVRLLGAYDSSYTTKMEQFLLKQEE  550
P. pastoris ADE2    SIVQMPRGVPVATVAINNAITNAALLAIRILGTIIDHKWQKEMSKYMNAMET  541

S. cerevisiae ADE2  EVLVKAQKLETVGYEAYLENK  571
P. pastoris ADE2    EVLGKASNLESEGYESYLKNRL  563
```

FIG. 1

YEAST STRAINS FOR PROTEIN PRODUCTION

This application is a continuation of U.S. patent application Ser. No. 12/744,959, filed May 27, 2010 which is the U.S. national phase filed under 35 U.S.C. § 371 of International Application No. PCT/US08/13719, filed Dec. 15, 2008 which claims the benefit of U.S. Provisional Patent Application No. 61/008,242, filed Dec. 19, 2007.

REFERENCE TO SEQUENCE LISTING SUBMITTED ELECTRONICALLY

The sequence listing of the present application is submitted electronically via EFS-Web as an ASCII formatted sequence listing with a file name "GFIBIO0030USPCT-SEQTXT-24 MAY 2010.txt", creation date of May 24, 2010, and a size of 34 KB. This sequence listing submitted via EFS-Web is part of the specification and is herein incorporated by reference in its entirety.

BACKGROUND OF THE INVENTION (1) Field of the Invention

The present invention relates to the field of molecular biology, in particular, the invention is concerned with novel selection genes to be used for improved protein production from transformed expression systems.

(2) Description of Related Art

In recent years the budding yeast *Pichia pastoris* has become a popular organism for the expression of heterologous proteins of academic and commercial interest (Cereghino et al., Curr. Opin. Biotechnol. 4: 329-332 (2002); Cereghino and Cregg, FEMS Microbiol. Rev. 24: 45-66 (2000). It was recently shown that it is possible to genetically modify the glycosylation machinery of *P. pastoris* and express heterologous glycoproteins decorated with complex type human glycans (Choi et al., Proc. Natl. Acad. Sci. 100: 5022-5027 (2003); Hamilton et al., Science 301: 1244-1246 (2003); Bobrowicz et al., Glycobiology 14: 757-766 (2004); Hamilton, Science, 313: 1441-1443 (2006). However, a need remains for methods and materials to achieve higher cellular productivity in transformed cell lines, such as transformed *P. pastoris* cell lines.

Over the years, numerous auxotrophic and dominant selectable markers have been developed (Higgins et al., Methods Mol. Biol. 103: 41-53 (1998); Lin Cereghino et al., Gene 263: 159-169 (2001); Nett and Gerngross, Yeast 20: 1279-1290 (2003); Nett et al., Yeast 22: 295-304 (2005) and used to construct protein expression vectors for various applications. Commonly, a gene of interest is integrated into the *P. pastoris* genome using a plasmid that is either linearized in the marker gene, another homologous region on the plasmid or in the AOX1 promoter fragment and transformed into the appropriate auxotrophic mutant. Homologous recombination of the free DNA termini then results in single-crossover type integration into these loci. Most *P. pastoris* transformants will contain a single copy of the expression vector, but to obtain transformants that express a high level of the protein of interest it is often desirable to screen for multi copy integrants. Using expression vectors that contain drug resistance genes as selection markers like Kan$^R$ or Zeo$^R$ it is possible to increase the number of transformants harboring multiple copies of the expression vector by increasing the level of drug used for selection. One significant disadvantage of the single-crossover type integration lies in the fact that the multiple integrated copies can collapse back into a single copy by homologous recombination. This can be especially problematic during scale-up of the expression reaction during fermentation if the protein of interest is toxic to the cells or the eviction of several copies of expression plasmid possesses other growth benefit for the cells.

U.S. Pat. No. 5,584,039 relates to a selectable marker gene ADE2 isolated from *Pichia methanolica*. Piontek et al., Appl Microbiol. Biotechnol. 50:331-338 (1998) relates to novel gene expression systems in *Schwanniomyces occidentalis* and *Pichia stipitis*, which systems utilize vectors containing an ADE2 marker and a putative replication sequence. However, no corresponding gene has previously been isolated from *Pichia pastoris*, and the effects of transformation with ADE2 in *P. pastoris* have not previously been identified.

Accordingly, a need exists for improved methods of transformation, selection and expression of heterogeneous genes using the *Pichia pastoris* yeast as the host expression system.

BRIEF SUMMARY OF THE INVENTION

The present invention provides methods and materials for the use of lower eukaryotic cells such as yeast or filamentous fungi as an expression system for expressing recombinant proteins.

In one aspect, the method is based on constructing slower growing ade2 auxotrophic strains of the lower eukaryote cells and using integration vectors that are capable of integrating into the genome of the ade2 auxotrophic strain and which comprises nucleic acids encoding an ADE2 marker gene or open reading frame (ORF) operably linked to a promoter and a recombinant protein, wherein the integration vector integrates into the genome of the ade2 auxotrophic strain, the ADE2 renders the auxotrophic strain prototrophic for adenine, and the recombinant protein is expressed.

Thus, provided is an expression system comprising (a) a *Pichia pastoris* host cell in which the endogenous ADE2 gene encoding Ade2p has been removed from the genome of the host cell; and (b) an integration vector comprising (1) a nucleic acid encoding the Ade2p; (2) a nucleic acid having an insertion site for the insertion of one or more expression cassettes comprising a nucleic acid encoding one or more heterologous peptides, proteins, and/or functional nucleic acids of interest, and (3) a targeting nucleic acid that directs insertion of the integration vector into a particular location of the genome of the host cell by homologous recombination.

Also, provided is a method for producing a recombinant *Pichia pastoris* host cell that expresses a heterologous protein or peptide comprising (a) providing the host cell in which the endogenous ADE2 gene encoding an Ade2p has been removed from the genome of the host cell; and (a) transforming the host cell with an integration vector comprising (1) a nucleic acid encoding the Ade2p; (2) a nucleic acid having one or more expression cassettes comprising a nucleic acid encoding one or more heterologous peptides, proteins, and/or functional nucleic acids of interest, and (3) a targeting nucleic acid that directs insertion of the integration vector into a particular location of the genome of the host cell by homologous recombination, wherein the transformed host cell produces the recombinant protein.

Further provided is an isolated nucleic acid comprising the ADE2 gene of *Pichia pastoris*. In particular aspects, the nucleic acid comprises the open reading frame that encodes the Ade2p protein or the nucleic acid has a nucleotide sequence with 95% identity to the nucleic acid sequence shown in SEQ ID NO:60 from nucleotide 127 to nucleotide 1,815. Further provided is an isolated polypeptide comprising an amino acid sequence with 95% identity to the amino acid sequence shown in SEQ ID NO:61.

The applicants further discovered that operably linking an auxotrophic marker gene or ORF to a minimal promoter in the integration vector, that is a promoter that has low transcriptional activity, enabled the production of recombinant host cells that contain a sufficient number of copies of the integration vector integrated into the genome of the auxotrophic host cell to render the cell prototrophic and which render the cells capable of producing amounts of the recombinant protein or functional nucleic acid of interest that are greater than the amounts that would be produced in a cell that contained only one copy of the integration vector integrated into the genome.

Therefore, provided is a method in which an auxotrophic strain of a lower eukaryote cell is obtained or constructed and an integration vector is provided that is capable of integrating into the genome of the auxotrophic strain and which comprises nucleic acids encoding a marker gene or ORF that compliments the auxotrophy and is operably linked to a weak promoter, an attenuated endogenous or heterologous promoter, a cryptic promoter, or a truncated endogenous or heterologous promoter and a recombinant protein. Host cells in which a number of the integration vectors have been integrated into the genome to compliment the auxotrophy of the host cell are selected in medium that lacks the metabolite that compliments the auxotrophy and maintained by propagating the host cells in medium that lacks the metabolite that compliments the auxotrophy or in medium that contains the metabolite because in that case, cells that evict the plasmids including the marker will grow more slowly.

In a further embodiment, provided is an expression system comprising (a) a host cell in which the endogenous gene encoding an auxotrophic selectable marker protein has been removed from the genome of the host cell; and (b) an integration vector comprising (1) a nucleic acid comprising an open reading frame (ORF) encoding a function that is complementary to the function of the endogenous gene encoding the auxotrophic selectable marker protein and which is operably linked to a weak promoter, an attenuated endogenous or heterologous promoter, a cryptic promoter, a truncated endogenous or heterologous promoter, or no promoter; (2) a nucleic acid having an insertion site for the insertion of one or more expression cassettes comprising a nucleic acid encoding one or more heterologous peptides, proteins, and/or functional nucleic acids of interest, and (3) a targeting nucleic acid that directs insertion of the integration vector into a particular location of the genome of the host cell by homologous recombination.

In a further still embodiment, provided is a method for expression of a recombinant protein in a host cell comprising (a) providing the host cell in which the endogenous gene encoding an auxotrophic selectable marker protein has been removed from the genome of the host cell; and (a) transforming the host cell with an integration vector comprising (1) a nucleic acid comprising an open reading frame (ORF) encoding a function that is complementary to the function of the endogenous gene encoding the auxotrophic selectable marker protein and which is operably linked to a weak promoter, an attenuated endogenous or heterologous promoter, a cryptic promoter, a truncated endogenous or heterologous promoter, or no promoter; (2) a nucleic acid having one or more expression cassettes comprising a nucleic acid encoding one or more heterologous peptides, proteins, and/or functional nucleic acids of interest, and (3) a targeting nucleic acid that directs insertion of the integration vector into a particular location of the genome of the host cell by homologous recombination, wherein the transformed host cell produces the recombinant protein.

In further aspects of the above embodiments, the auxotrophic selectable marker protein is encoded by a gene selected from the group consisting of ADE, URA, and LYS. In a further still aspect, the auxotrophic selectable marker protein is encoded by the ADE1 gene or the ADE2 gene.

In further still aspects, the integration vector comprises multiple insertion sites for the insertion of one or more expression cassettes encoding the one or more heterologous peptides, proteins and/or functional nucleic acids of interest. In further still aspects, the integration vector comprises more than one expression cassette. In further still aspects, the integration vector comprises little or no homologous DNA sequence between the expression cassettes. In further still aspects, the integration vector comprises a first expression cassette encoding a light chain of a monoclonal antibody and a second expression cassette encoding a heavy chain of a monoclonal antibody.

In further still aspects, the host cell is a lower eukaryote. In further still aspects, the host cell is from a species selected from the group consisting of *Pichia pastoris*, *Pichia finlandica*, *Pichia trehalophila*, *Pichia koclamae*, *Pichia membranaefaciens*, *Pichia minuta* (*Ogataea minuta*, *Pichia lindneri*), *Pichia opuntiae*, *Pichia thermotolerans*, *Pichia salictaria*, *Pichia guercuum*, *Pichia pijperi*, *Pichia stiptis*, *Pichia methanolica*, *Pichia* sp., *Saccharomyces cerevisiae*, *Saccharomyces* sp., *Hansenula polymorpha*, *Kluyveromyces* sp., *Kluyveromyces lactis*, *Candida albicans*, *Aspergillus nidulans*, *Aspergillus niger*, *Aspergillus oryzae*, *Trichoderma reesei*, *Chrysosporium lucknowense*, *Fusarium* sp., *Fusarium gramineum*, *Fusarium venenatum*, *Physcomitrella patens*, and *Neurospora crassa*. In further still aspects, the expression system of claim 1, wherein the host cell is *Pichia pastoris* or a *Pichia pastoris* cell that has been modified to be capable of producing glycoproteins having hybrid or complex N-glycans.

DEFINITIONS

Unless otherwise defined herein, scientific and technical terms and phrases used in connection with the present invention shall have the meanings that are commonly understood by those of ordinary skill in the art. Further, unless otherwise required by context, singular terms shall include the plural and plural terms shall include the singular. Generally, nomenclatures used in connection with, and techniques of biochemistry, enzymology, molecular and cellular biology, microbiology, genetics and protein and nucleic acid chemistry and hybridization described herein are those well known and commonly used in the art. The methods and techniques of the present invention are generally performed according to conventional methods well known in the art and as described in various general and more specific references that are cited and discussed throughout the present specification unless otherwise indicated. See, e.g., Sambrook et al. Molecular Cloning: A Laboratory Manual, 2d ed., Cold Spring Harbor Laboratory Press, Cold Spring Harbor, N.Y. (1989); Ausubel et al., Current Protocols in Molecular Biology, Greene Publishing Associates (1992, and Supplements to 2002); Harlow and Lane, Antibodies: A Laboratory Manual, Cold Spring Harbor Laboratory Press, Cold Spring Harbor, N.Y. (1990); Taylor and Drickamer, Introduction to Glycobiology, Oxford Univ. Press (2003); Worthington Enzyme Manual, Worthington Biochemical Corp., Freehold, N.J.; Handbook of Biochemistry: Section A Proteins, Vol I, CRC Press (1976); Handbook of Biochemistry: Section A Proteins, Vol II, CRC Press (1976); Essentials of Glycobiology, Cold Spring Harbor Laboratory Press (1999). All publications, patents and other references mentioned herein are hereby incorporated by reference in their entireties.

The genetic nomenclature for naming chromosomal genes of yeast is used herein. Each gene, allele, or locus is designated by three italicized letters. Dominant alleles are denoted by using uppercase letters for all letters of the gene symbol, for example, ADE2 for the adenine 2 gene, whereas lowercase letters denote the recessive allele, for example, the auxotrophic marker for adenine 2, ade2. Wild-type genes are denoted by superscript "+" and mutants by a "−" superscript. The symbol Δ can denote partial or complete deletion. Insertion of genes follow the bacterial nomenclature by using the symbol "::", for example, trp2::ARG2 denotes the insertion of the ARG2 gene at the TRP2 locus, in which ARG2 is dominant (and functional) and trp2 is recessive (and defective). Proteins encoded by a gene are referred to by the relevant gene symbol, non-italicized, with an initial uppercase letter and usually with the suffix 'p", for example, the adenine 2 protein encoded by ADE2 is Ade2p. Phenotypes are designated by a non-italic, three letter abbreviation corresponding to the gene symbol, initial letter in uppercase. Wild-type strains are indicated by a "+" superscript and mutants are designated by a "−" superscript. For example, Ade2$^+$ is a wild-type phenotype whereas Ade2$^-$ is an auxotrophic phenotype (requires adenine).

The term "vector" as used herein is intended to refer to a nucleic acid molecule capable of transporting another nucleic acid to which it has been linked. One type of vector is a "plasmid", which refers to a circular double stranded DNA loop into which additional DNA segments may be ligated. Other vectors include cosmids, bacterial artificial chromosomes (BAC) and yeast artificial chromosomes (YAC). Another type of vector is a viral vector, wherein additional DNA segments may be ligated into the viral genome (discussed in more detail below). Certain vectors are capable of autonomous replication in a host cell into which they are introduced (e.g., vectors having an origin of replication which functions in the host cell). Other vectors can be integrated into the genome of a host cell upon introduction into the host cell, and are thereby replicated along with the host genome. Moreover, certain preferred vectors are capable of directing the expression of genes to which they are operatively linked. Such vectors are referred to herein as "recombinant expression vectors" (or simply, "expression vectors").

The term "integration vector" refers to a vector that can integrate into a host cell and which carries a selection marker gene or open reading frame (ORF), a targeting nucleic acid, one or more genes or nucleic acids of interest, and a nucleic acid sequence that functions as a microorganism autonomous DNA replication start site, herein after referred to as an origin of DNA replication, such as ORI for bacteria. The integration vector can only be replicated in the host cell if it has been integrated into the host cell genome by a process of DNA recombination such as homologous recombination that integrates a linear piece of DNA into a specific locus of the host cell genome. For example, the targeting nucleic acid targets the integration vector to the corresponding region in the genome where it then by homologous recombination integrates into the genome.

The term "selectable marker gene", "selection marker gene", "selectable marker sequence" or the like refers to a gene or nucleic acid sequence carried on a vector that confers to a transformed host a genetic advantage with respect to a host that does not contain the marker gene. For example, the P. pastoris URA5 gene is a selectable marker gene because its presence can be selected for by the ability of cells containing the gene to grow in the absence of uracil. Its presence can also be selected against by the inability of cells containing the gene to grow in the presence of 5-FOA. Selectable marker genes or sequences do not necessarily need to display both positive and negative selectability. Non-limiting examples of marker sequences or genes from P. pastoris include ADE1, ADE2 ARG4, HIS4, LYS2, URA5, and URA3. In general, a selectable marker gene as used the expression systems disclosed herein encodes a gene product that complements an auxotrophic mutation in the host. An auxotrophic mutation or auxotrophy is the inability of an organism to synthesize a particular organic compound or metabolite required for its growth (as defined by IUPAC). An auxotroph is an organism that displays this characteristic; auxotrophic is the corresponding adjective. Auxotrophy is the opposite of prototrophy.

The term "a targeting nucleic acid" refers to a nucleic acid carried on the vector plasmid that directs the insertion by homologous recombination of the vector integration plasmid into a specific homologous locus in the host called the "target locus".

The term "sequence of interest" or "gene of interest" or "nucleic acid of Interest" refers to a nucleic acid sequence, typically encoding a protein or a functional RNA, that is not normally produced in the host cell. The methods disclosed herein allow efficient expression of one or more sequences of interest or genes of interest stably integrated into a host cell genome. Non-limiting examples of sequences of interest include sequences encoding one or more polypeptides having an enzymatic activity, e.g., an enzyme which affects N-glycan synthesis in a host such as mannosyltransferases, N-acetylglucosaminyltransferases, UDP-N-acetylglucosamine transporters, galactosyltransferases, UDP-N-acetylgalactosyltransferase, sialyltransferases, fucosyltransferases, erythropoietin, cytokines such as interferon-α, interferon-β, interferon-γ, interferon-ω, and granulocyte-CSF, coagulation factors such as factor VIII, factor IX, and human protein C, soluble IgE receptor α-chain, IgG, IgM, urokinase, chymase, urea trypsin inhibitor, IGF-binding protein, epidermal growth factor, growth hormone-releasing factor, annexin V fusion protein, angiostatin, vascular endothelial growth factor-2, myeloid progenitor inhibitory factor-1, and osteoprotegerin.

The term "operatively linked" refers to a linkage in which a expression control sequence is contiguous with the gene or sequence of interest or selectable marker gene or sequence to control expression of the gene or sequence, as well as expression control sequences that act in trans or at a distance to control the gene of interest.

The term "expression control sequence" as used herein refers to polynucleotide sequences which are necessary to affect the expression of coding sequences to which they are operatively linked. Expression control sequences are sequences which control the transcription, post-transcriptional events, and translation of nucleic acid sequences. Expression control sequences include appropriate transcription initiation, termination, promoter, and enhancer sequences; efficient RNA processing signals such as splicing and polyadenylation signals; sequences that stabilize cytoplasmic mRNA; sequences that enhance translation efficiency (e.g., ribosome binding sites); sequences that enhance protein stability; and when desired, sequences that enhance protein secretion. The nature of such control sequences differs depending upon the host organism; in prokaryotes, such control sequences generally include promoter, ribosomal binding site, and transcription termination sequence. The term "control sequences" is intended to include, at a minimum, all components whose presence is essential for expression, and can also include additional components whose presence is advantageous, for example, leader sequences and fusion partner sequences.

The term "recombinant host cell" ("expression host cell," "expression host system," "expression system" or simply "host cell"), as used herein, is intended to refer to a cell into which a recombinant vector has been introduced. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein. A recombinant host cell may be an isolated cell or cell line grown in culture or may be a cell which resides in a living tissue or organism.

The term "eukaryotic" refers to a nucleated cell or organism, and includes insect cells, plant cells, mammalian cells, animal cells, and lower eukaryotic cells.

The term "lower eukaryotic cells" includes yeast, unicellular and multicellular or filamentous fungi. Yeast and fungi include, but are not limited to Pichia pastoris, Pichia finlandica, Pichia trehalophila, Pichia koclamae, Pichia membranaefaciens, Pichia minuta (Ogataea minuta, Pichia lindneri), Pichia opuntiae, Pichia thermotolerans, Pichia salictaria, Pichia guercuum, Pichia pijperi, Pichia stiptis, Pichia methanolica, Pichia sp., Saccharomyces cerevisiae, Saccharomyces sp., Hansenula polymorpha, Kluyveromyces sp., Kluyveromyces lactis, Candida albicans, Aspergillus nidulans, Aspergillus niger, Aspergillus oryzae, Trichoderma reesei, Chrysosporium lucknowense, Fusarium sp., Fusarium gramineum, Fusarium venenatum, Physcomitrella patens, and Neurospora crassa.

The term "peptide" as used herein refers to a short polypeptide, e.g., one that is typically less than about 50 amino acids long and more typically less than about 30 amino acids long. The term as used herein encompasses analogs, derivatives, and mimetics that mimic structural and thus, biological function of polypeptides and proteins.

The term "polypeptide" encompasses both naturally-occurring and non-naturally-occurring proteins, and fragments, mutants, derivatives and analogs thereof. A polypeptide may be monomeric or polymeric. Further, a polypeptide may comprise a number of different domains each of which has one or more distinct activities.

The term "fusion protein" refers to a polypeptide comprising a polypeptide or fragment coupled to heterologous amino acid sequences. Fusion proteins are useful because they can be constructed to contain two or more desired functional elements from two or more different proteins. A fusion protein comprises at least 10 contiguous amino acids from a polypeptide of interest, more preferably at least 20 or 30 amino acids, even more preferably at least 40, 50 or 60 amino acids, yet more preferably at least 75, 100 or 125 amino acids. Fusions that include the entirety of the proteins of the present invention have particular utility. The heterologous polypeptide included within the fusion protein of the present invention is at least 6 amino acids in length, often at least 8 amino acids in length, and usefully at least 15, 20, and 25 amino acids in length. Fusions also include larger polypeptides, or even entire proteins, such as the green fluorescent protein (GFP) chromophore-containing proteins having particular utility. Fusion proteins can be produced recombinantly by constructing a nucleic acid sequence which encodes the polypeptide or a fragment thereof in frame with a nucleic acid sequence encoding a different protein or peptide and then expressing the fusion protein. Alternatively, a fusion protein can be produced chemically by crosslinking the polypeptide or a fragment thereof to another protein.

The term "functional nucleic acid" refers to a nucleic acid molecule that, upon introduction into a host cell or expression in a host cell, specifically interferes with expression of a protein. In general, functional nucleic acid molecules have the capacity to reduce expression of a protein by directly interacting with a transcript that encodes the protein. Ribozymes, antisense nucleic acids, and siRNA molecules, including shRNA molecules, short RNAs (typically less than 400 bases in length), and micro-RNAs (miRNAs) constitute exemplary functional nucleic acids.

Unless otherwise defined, all technical and scientific terms used herein have the same meaning as commonly understood by one of ordinary skill in the art to which this invention pertains. Exemplary methods and materials are described below, although methods and materials similar or equivalent to those described herein can also be used in the practice of the present invention and will be apparent to those of skill in the art. All publications and other references mentioned herein are incorporated by reference in their entirety. In case of conflict, the present specification, including definitions, will control. The materials, methods, and examples are illustrative only and not intended to be limiting.

BRIEF DESCRIPTION OF THE DRAWINGS

FIG. 1 shows an alignment of the *P. pastoris* Ade2p amino acid sequence (SEQ ID NO:61) to the *S. cerevisiae* Ade2p amino acid sequence (SEQ ID NO:62).

DETAILED DESCRIPTION OF THE INVENTION

Figure 2A:
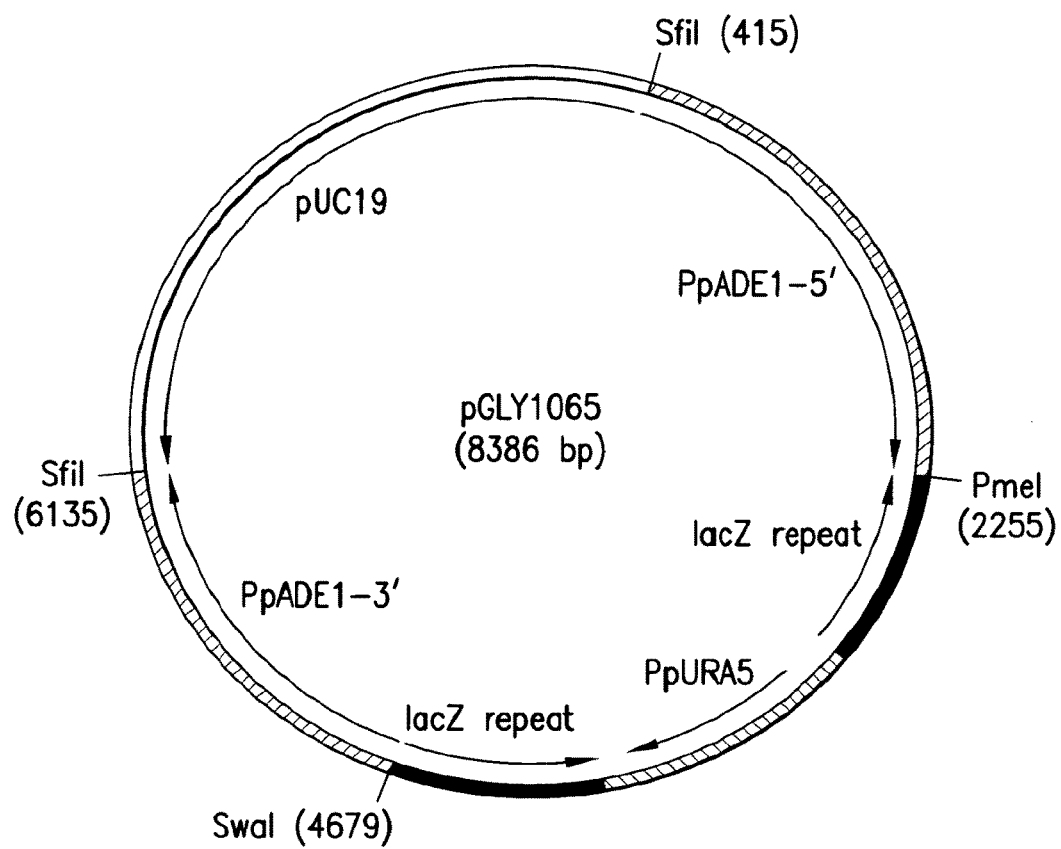
FIG. 2A shows a map of plasmid pGLY1065.
Figure 2B:
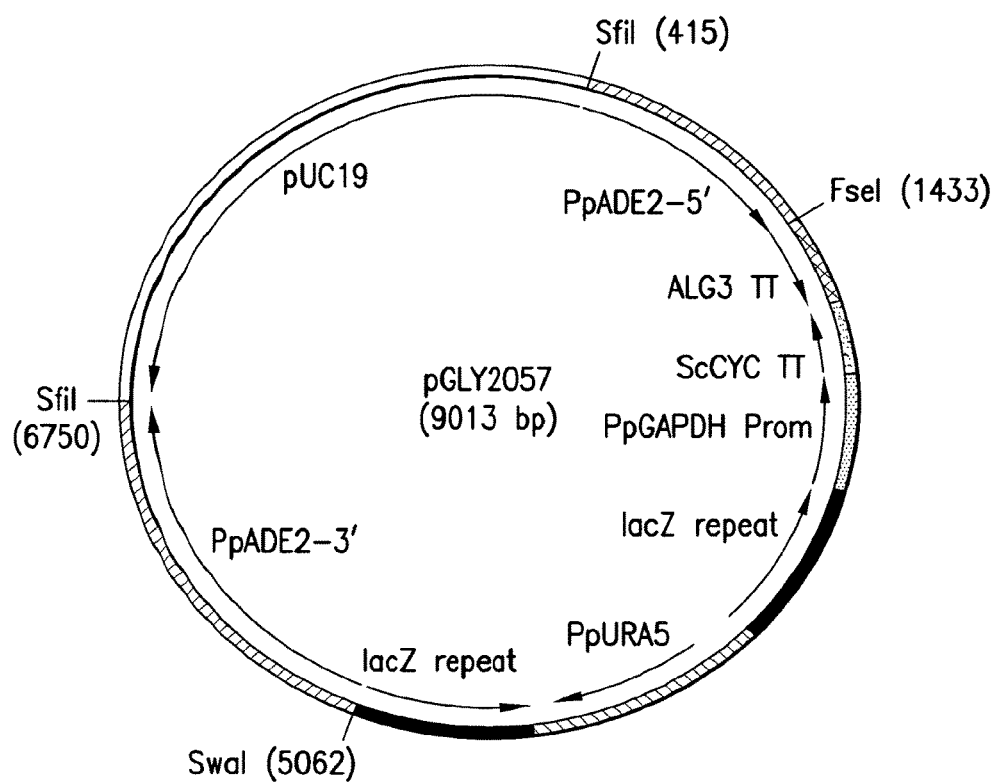
FIG. 2B shows a map of plasmid pGLY2057.
Figure 2C:
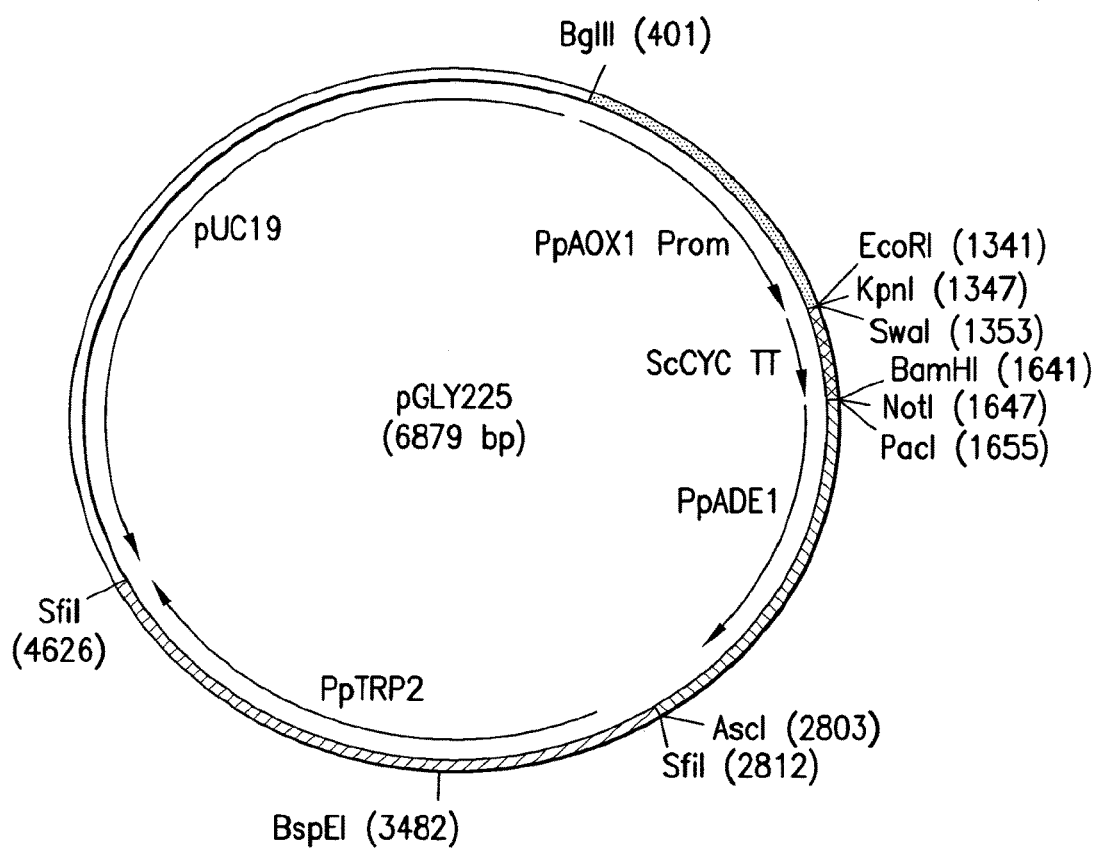
FIG. 2C shows a map of plasmid pGLY225.
Figure 2D:
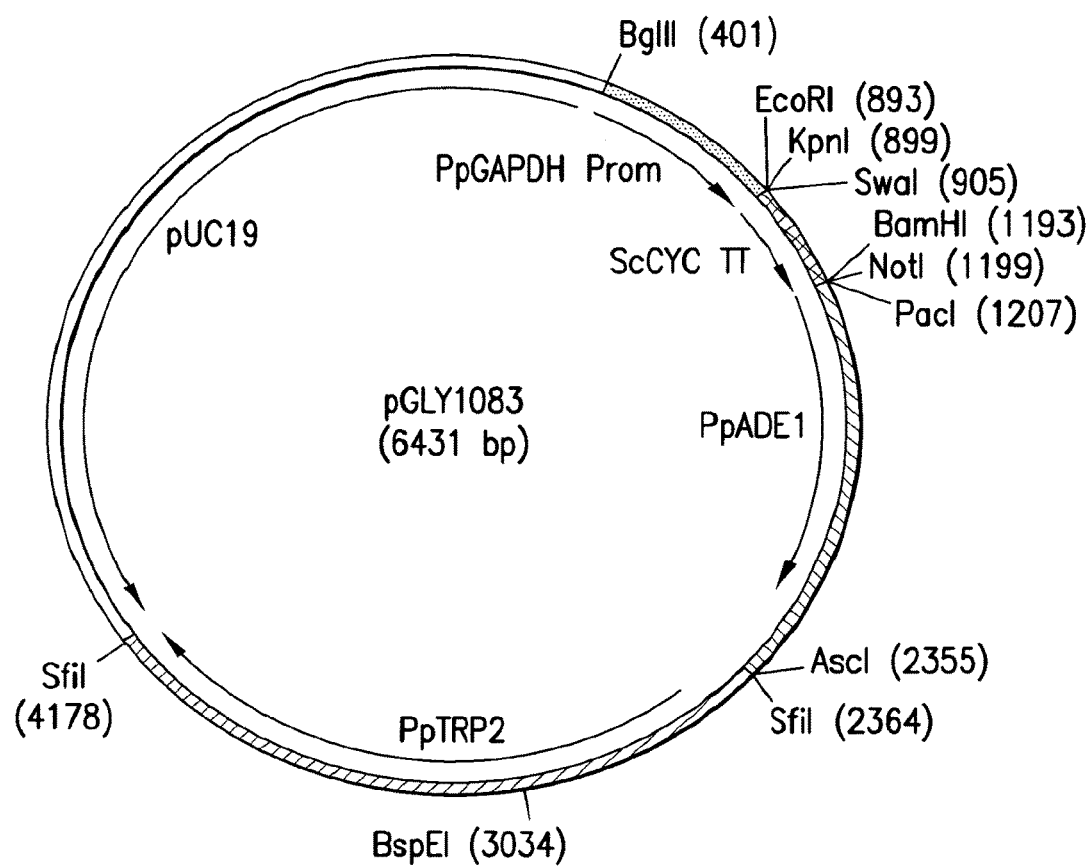
FIG. 2D shows a map of plasmid pGLY1083.
Figure 2E:
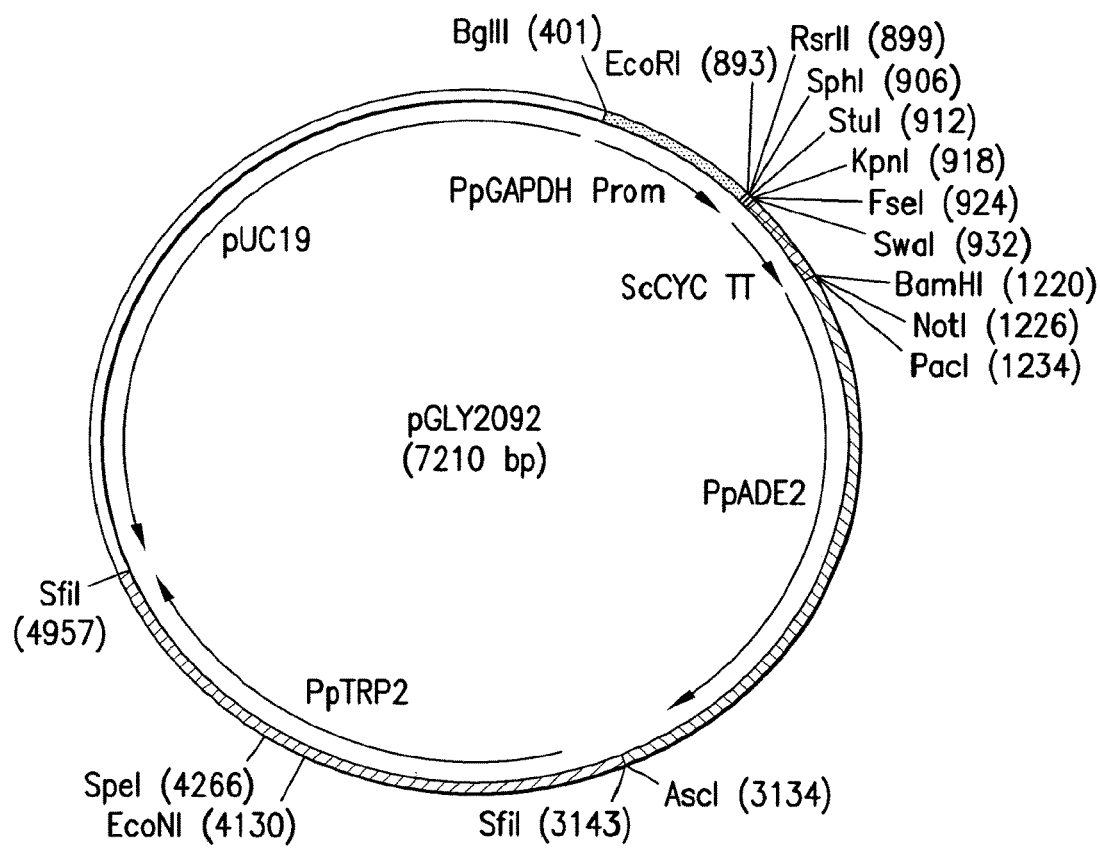
FIG. 2E shows a map of plasmid pGLY2092.
Figure 2F:
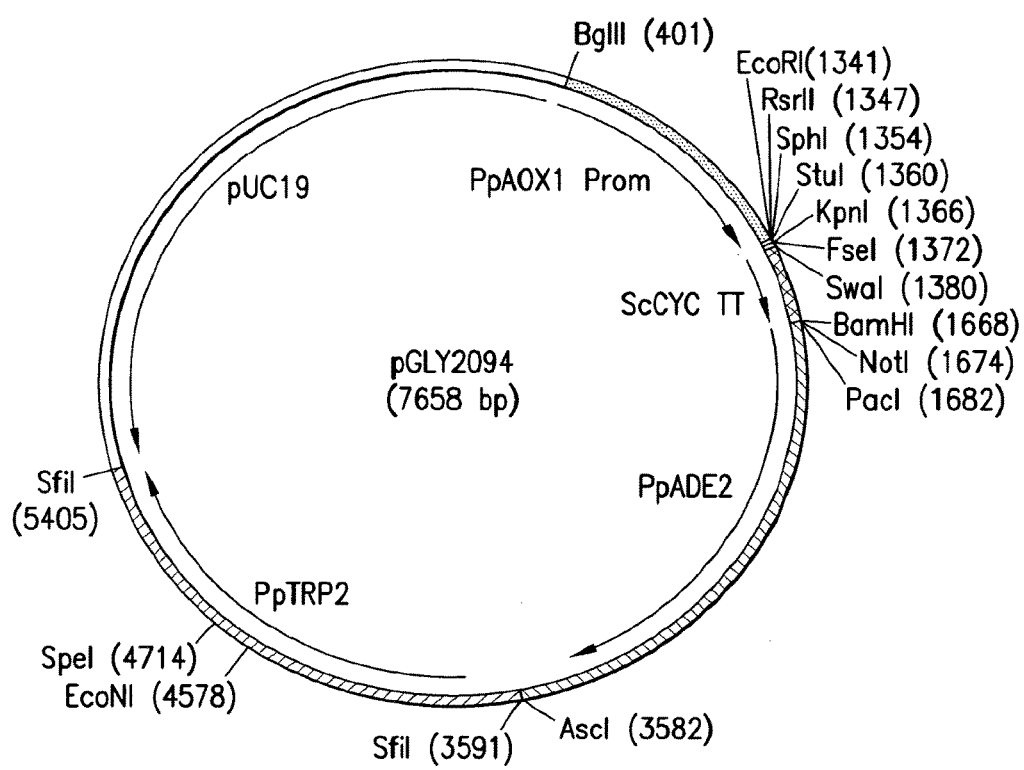
FIG. 2F shows a map of plasmid pGLY2094.

The present invention provides methods and materials for the use of lower eukaryotic cells such as yeast or filamentous fungi as an expression system for expressing recombinant peptides, proteins, or functional nucleic acids. In one aspect, the method provides a method for expressing a recombinant protein comprising obtaining or constructing slower growing ade2 auxotrophic strains of the lower eukaryote cells and introducing into the cells integration vectors that are capable of integrating into the genome of the ade2 auxotrophic strain and which comprises a nucleic acid encoding an ADE2 marker gene or open reading frame (ORF) operably linked to a promoter and a nucleic acid expressing a recombinant protein or functional nucleic acid of interest, wherein the integration vector integrates into the genome of the ade2 auxotrophic strain, the ADE2 renders the auxotrophic strain prototrophic for adenine and the recombinant peptide, protein, or functional nucleic acid is expressed. The recombinant host cells are selected for in medium that lacks the metabolite adenine but can be maintained in medium that lacks the metabolite adenine or in medium that includes the metabolite adenine. In general, those recombinant host cells that might lose the ADE2 marker (revertants) will grow more slowly and will be lost over time as the recombinant cells are grown. The loss of revertants over time will occur whether the recombinant host cells are grown in medium that includes the metabolite adenine or in medium that either lacks the metabolite adenine.

In developing the above invention, the applicants discovered that when the integration vector for introducing a recombinant protein into a lower eukaryote host cell that is auxotrophic for a particular marker gene includes in the integration vector a nucleic acid encoding the complimentary marker gene or ORF but wherein the marker gene or ORF is operably linked to a weak, attenuated, cryptic, truncated promoter that reduces the native activity of the promoter to level less than the native promoter, or no promoter, the auxotrophy of the host cell can be complimented provided that more than one copy of the integration vector is integrated into the genome of the host cell. Because the recombinant host cell contains more than one copy of the integration vector and each copy of the integration vector is transcriptionally active, the recombinant host cell is capable of producing a sufficient quantity of the marker gene or ORF to render the host cell prototrophic for the auxotrophic marker and thus capable of growing in medium that lacks the metabolite that can compliment the auxotrophy. The weaker the promoter linked to the complimentary marker gene or ORF, the more copies of the integration vector integrated into the genome of the host cell that are needed to render the host cell prototrophic for the auxotrophic marker. Host cells that lose copies of the integration vector integrated into the host genome during cell growth or passage in medium that lack the metabolite that can compliment the auxotrophy are rendered auxotrophic again for the marker gene. These newly auxotrophic host cells are at a selective disadvantage in the culture medium and in general, are lost as the remaining prototrophic host cells continue to grow and replicate. Importantly, because the integration vector contains an expression cassette that expresses one or more recombinant proteins or functional nucleic acids of interest, host cells containing one or more copies of the integration vector will produce more of the recombinant protein than would be produced in host cells that contained only one copy of the integration vector.

Therefore, methods, materials, and systems that are particularly useful for producing recombinant host cells that are capable of producing large quantities of recombinant proteins (including peptides), or functional nucleic acids are provided. Thus, the present invention provides a method in which an auxotrophic strain of a lower eukaryote cell is obtained or constructed and an integration vector is provided that is capable of integrating into the genome of the auxotrophic strain and which comprises nucleic acids encoding a marker gene or ORF that compliments the auxotrophy and is either operably linked to a weak, cryptic, attenuated, or truncated promoter or no promoter and a recombinant protein. Host cells in which a number of the integration vectors have been integrated into the genome to compliment the auxotrophy of the host cell are selected in medium that lacks the metabolite that compliments the auxotrophy and maintained by propagating the host cells in medium that either lacks the metabolite that compliments the auxotrophy or includes the metabolite that compliments the auxotrophy. In general, those recombinant host cells that might lose the auxotrophic marker (revertants) will grow more slowly and will be lost over time as the recombinant cells are grown. The loss of revertants over time will occur whether the recombinant host cells are grown in medium that includes the metabolite or in medium that either lacks the metabolite. This phenomenon has been observed at least for the auxotrophic markers ADE, URA, or LYS and is currently believed to be due at least in part to poor transport of the metabolite from the medium into the recombinant host cell.

In a general aspect, recombinant host cells are rendered auxotrophic for a particular organic compound by removing or deleting the gene or locus encoding the gene product necessary for producing the organic compound or an intermediate for producing the organic compound or metabolite. The auxotrophic host cells are then transformed with an integration vector that comprises (1) a nucleic acid comprising an open reading frame (ORF) encoding a selectable marker gene or other nucleic acid that complements the auxotrophy; (2) a nucleic acid encoding one or more ORFs encoding a heterologous or recombinant protein or peptide or expressing a functional nucleic acid of interest; and (3) nucleic acid comprising a targeting sequence that directs insertion of the integration vector into a particular target location or locus of the genome of the host cell by homologous recombination.

The targeting sequence in the plasmid can comprise any sequence within the host cell genome such as a host cell gene, a host cell promoter or terminator sequence, or a sequence of unknown function. For integrating into a host cell promoter or termination sequence, the promoter and/or the terminator sequence in the expression cassette used for regulating expression of the one or more ORFs encoding a heterologous or recombinant protein or peptide or expressing a functional nucleic acid of interest can also function as the targeting sequence for targeting the integration vector to the target location. For example, the nucleic acid of (1) or (2) above can be operably linked to a host cell promoter for a host cell gene adjacent to the promoter to which the integration vector is targeted. Integration of the vector into the promoter via roll-in single crossover homologous recombination results in a duplication of the promoter sequences. Thus, after integration, the expression cassette is still operably linked to the promoter comprising the targeting sequence and the host cell gene adjacent to the promoter that was the targeting sequence is still operable. Thus, in the recombinant host cell, expression of a heterologous protein, peptide, or functional nucleic is effected without disrupting expression of the host cell gene adjacent to the targeting site.

To integrate the integration vector into the genome of a host cell by roll-in single crossover homologous recombination, the vector is linearized by cleaving the integration vector at a site within the targeting sequence so as to produce a linear nucleic acid molecule in which the targeting sequences are at the ends of the molecule. Single cross-over events lead to a duplication of the genomic locus and generates direct repeats. While these direct repeats display a high recombination rate and can result in the loss of the marker and expression cassette during propagation of the recombinant host cell, the method disclosed herein where the marker is operably linked to a weak, cryptic, attenuated, or truncated promoter or no promoter ensures that only host cells that maintain the copy number of integration vectors sufficient to render the host cell prototrophic for the marker during propagation. In a preferred aspect, the integration vector is linearized at a restriction enzyme site that occurs only once in the targeting sequence. The vector then integrates into the target site by roll-in single crossover homologous recombination. Roll-in single crossover homologous recombination enables integration of the integration vector into the genome without disrupting expression of the gene at the target site. Roll-in single crossover homologous recombination has been described in Nett et al., Yeast 22: 295-304 (2005).

An important feature of the integration vector is that the ORF encoding the selectable marker gene or other nucleic acid is not operably linked to its endogenous full-strength promoter or to a heterologous full-strength promoter but to a weak promoter, an attenuated endogenous or heterologous promoter, a cryptic promoter, or a truncated endogenous or heterologous promoter in which the truncation renders the promoter with a transcription activity that is less than the native promoter. In particular embodiments, the attenuated or truncated promoter has a transcription activity that is no more than 50% of the activity of the full-strength promoter. In further embodiments, the attenuated or truncated promoter has a transcription activity that is no more than 10% of the activity of the full-strength promoter. In further embodiments, the attenuated or truncated promoter has a transcription activity that is no more than 1% of the activity of the full-strength promoter. While not wishing to be bound by any theory, it is believed that in general, the nucleic acid sequence adjacent to the ORF encoding the selectable marker gene will contain a so-called cryptic promoter that enables a low level of expression of the selectable marker gene. A cryptic promoter will allow a sufficient amount of spurious transcription initiation adjacent to the ORF sufficient to produce a low amount of the selectable marker. Since expression of the selectable marker gene is below the level needed to fully complement the auxotrophy, multiple integrations of the integration vector into the target sequence in the host cell is necessary for full complementation of the auxotrophy. Because multiple copies of the integration vector must be integrated into the genome of the host cell to complement the auxotrophy, there are multiple copies of the ORF encoding the protein or peptide or functional nucleic acid of interest, all of which are expressed. Thus, the host cell is capable of encoding more of the protein or peptide or functional nucleic acid of interest than a host cell that includes only one copy of the integration vector integrated into its genome.

In practicing the method, it is preferable that there not be any of the selectable marker gene sequence in the auxotrophic host cell that could compete with the targeting sequence for integration. Thus, in further embodiments, either the entire gene encoding the marker (including upstream and downstream regions) is deleted or removed from the genome or at least the open reading frame encoding the marker gene is deleted or removed from the genome. Stable recombinant host cells in which the integration vector is integrated into the target locus are selected by cultivating the transformed host cells in a culture medium that lacks the particular organic compound (metabolite). Because the selectable marker gene or ORF is not operably linked to an endogenous or heterologous full-strength promoter but is operably linked to a weak, attenuated, cryptic promoter, or truncated promoter (or in particular aspects, no promoter), the recombinant, transformed host cells containing only one copy of the integration vector inserted into the target locus are not rendered prototrophic for the organic compound or metabolite. For the transformed host cells to be rendered prototrophic for the organic compound or metabolite, multiple copies of the integration vector must be integrated into the target locus for the host cell. In addition, because multiple copies of the integration vector must be integrated into the target locus, significant quantities of the protein or peptide encoded by the gene or sequence of interest are also produced.

Lower eukaryotes such as yeast are preferred for expression of proteins because they can be economically cultured, give high yields, and when appropriately modified are capable of suitable glycosylation. Yeast particularly offers established genetics allowing for rapid transformations, tested protein localization strategies and facile gene knock-out techniques. Suitable vectors have expression control sequences, such as promoters, including 3-phosphoglycerate kinase or other glycolytic enzymes, and an origin of replication, termination sequences and the like as desired.

Various yeasts, such as *K. lactis, Pichia pastoris, Pichia methanolica*, and *Hansenula polymorpha* are generally preferred for cell culture because they are able to grow to high cell densities and secrete large quantities of recombinant protein. Likewise, filamentous fungi, such as *Aspergillus niger, Fusarium* sp, *Neurospora crassa* and others can be used to produce glycoproteins of the invention at an industrial scale. Other cells useful as host cells in the present invention include prokaryotic cells, such as *E. coli*, and eukaryotic host cells in cell culture, including lower eukaryotic cells, plant cells, and mammalian cells, such as Chinese Hamster Ovary (CHO).

Lower eukaryotes, particularly yeast, can be genetically modified so that they express glycoproteins in which the glycosylation pattern is human-like or humanized. Such can be achieved by eliminating selected endogenous glycosylation enzymes and/or supplying exogenous enzymes as described by Gerngross et al., US 2004/0018590, the disclosure of which is hereby incorporated herein by reference. For example, a host cell can be selected or engineered to be depleted in 1,6-mannosyl transferase activities, which would otherwise add mannose residues onto the N-glycan on a glycoprotein.

U.S. Published application No. 20070072262 discloses ARG1, ARG2, ARG3, HIS1, HIS2, HIS5, and HIS6 genes and methods of using the genes for stable genetic integration into yeast and U.S. published application No. 20040229306 discloses the *Pichia pastoris* URA5 gene and its use for genetic stable integration in yeast. Selectable marker genes that are particularly useful in practicing the methods and systems herein include, but are not limited to, URA3, URA5, HIS3, LEU2, TRP1, LYS2, ADE1, and ADE2 loci. Useful are auxotrophic host cells and selectable marker genes in which the particular auxotrophy renders the cell less able to compete with or grow more slowly than the corresponding prototroph. Thus, particularly useful selectable marker genes are the selectable marker genes ADE1, ADE2. LYS2, URA3, and URA5.

The ADE1 gene has been cloned from various species of yeast and fungi, including *Saccharomyces cerevisiae* (Myasnikov et al., Gene, 109:143-147 (1991); *Kluyveromyces lactis* (Zonneveld and van der Zanden, et al., Yeast, 11:823-827 (1995), *Pichia pastoris* (Cereghino et al., Gene 263: 159-169 (2001)). ADE1 gene encodes N-succinyl-5-aminoimidazole-4-carboxamide ribotide (SAICAR) synthetase, which is required for de novo purine nucleotide biosynthesis. Red pigment accumulates in mutant cells deprived of adenine.

The ADE2 gene has been cloned from various species of yeast and fungi, including *Saccharomyces cerevisiae* (Jones and Fink, "Regulation of amino acid and nucleotide biosynthesis in yeast" pp. 181-299 in The Molecular Biology of the Yeast *Saccharomyces*: Metabolism and Gene Expression, Strathern et al. (Eds.) Cold Spring Harbor, N.Y.: Cold Spring Harbor Laboratory Press); *Candida albicans* (Kurtz et al., Mol. Cell. Biol., 6:142-149 (1986)); *Aspergillus oryzae*, (Jin et al., Biosci Biotechnol Biochem. 68:656-62 (2004), and *Pichia pastoris* (herein). The ADE2 gene encodes phosphoribosyl-aminoimidazole carboxylase, which catalyzes a step in the de novo purine nucleotide biosynthetic pathway. Red pigment accumulates in mutant cells deprived of adenine.

In further embodiments, a cell line can be transformed with a vector that will displace or knock out the function of one or more auxotrophic genes, for example, knocking out or displacing the ADE1 or ADE2 genes to render the cells auxotrophic for adenine, for example, cells with an Ade1⁻ or Ade2⁻ phenotype. Thus, the present invention includes methods for genetically engineering cell lines such that they contain auxotrophic mutations which impede the growth of the cells. These cell lines containing auxotrophic mutations can then serve as the host cells for selection as taught herein, in which the host cells are transformed with integration vectors encoding one or more desired glycoproteins and genes which complement the auxotrophic mutations such that the cells expressing the desired protein(s) will also carry the gene(s) which complement the auxotrophic mutations and provide a phenotype which is readily identifiable and selectable.

The method disclosed herein using the ADE1 or ADE2 markers and ade1 or ade2 auxotrophic host cells is particularly useful for making recombinant *Pichia pastoris* host cells because it addresses the scarcity of suitable markers for *Pichia pastoris* that can be used for multicopy selection. To date, primarily dominant markers, like Zeocin, are used for this purpose. However, dominant markers possess significant disadvantages. For example, during fermentation, it is frequently not feasible to add the antibiotic, in order to make sure all integrated copies of the heterologous gene stay integrated. However, if the constructs disclosed herein are evicted, the cells will become unable to produce adenine and will exhibit the selectable phenotype of slower growth and pinkish color. Therefore, heterologous constructs which are evicted during fermentation are easily selected against by virtue of this slower growth.

The advantages of the disclosed system are the ability to select transformants with multiple copies of the marker and desired gene for expression in the host cell integrated in the genome by color, and the stable retention of the transformants with one or more copies integrated into the genome because of the slow growth of ade1 or ade2 cells. In one aspect, the system utilizes the differential phenotypes of pink/white color selection of ade/ADE strains coupled with the slow growth of strains having an Ade1⁻ or Ade2⁻ phenotype and the integration of a plasmid comprising a copy of the ADE1 or ADE2 open reading frame (ORF) operably linked to a promoter and a desired gene for expression in the host cell in order to in order to provide a system that is an improvement over the current system for making recombinant host cells that relies upon dominant Zeocin selection. In another aspect, the system utilizes the differential phenotypes of pink/white color selection of ade/ADE strains coupled with the slow growth of strains having an Ade1⁻ or Ade2⁻ phenotype and the forced multiple integration of a plasmid comprising a copy of the ADE1 or ADE2 ORF operably linked to a weak, attenuated, or cryptic promoter and a desired gene for expression in the host cell in order to provide a system that is an improvement over the current system for making recombinant host cells that relies upon dominant Zeocin selection. Thus, the methods and materials are useful for stable high level expression of heterologous proteins.

Thus, in particular embodiments, the method and system comprises recombinant host cells, non-human eukaryotic host cells, in particular lower eukaryotic host cells such as yeast and filamentous fungal host cells, with improved productivity for the production of recombinant proteins, including glycoproteins when using host cells capable of making glycoproteins having hybrid or complex N-glycans. The recombinant host cells are modified by the reduction or elimination of the function of at least one endogenous gene encoding an auxotrophic marker gene, such as ADE1 or ADE2. Cells with a mutation leading to adenine deficiency grow quite slowly, and accumulate a reddish pigment, which results in production of pink colonies (that is, cells with an Ade1⁻ or Ade2⁻ phenotype). When these cells with an Ade1⁻ or Ade2⁻ phenotype are transformed with a plasmid comprising an ADE1 or ADE2 ORF, respectively, operably linked to a promoter for expressing the ADE1 or ADE2 ORF, the Ade1 or Ade2 mutation is complemented and the cell is rendered prototrophic for adenine, that is, the cells are rendered to have an Ade1⁺ or Ade2⁺ phenotype. These complemented recombinant cells exhibit a white color and large colony size, which facilitates identification and selection of the recombinant cells. Alternatively, when these cells with an Ade1⁻ or Ade2⁻ phenotype are transformed with a plasmid comprising the ADE1 or ADE2 ORF, respectively, not operably linked to a promoter for expressing the ADE1 or ADE2 ORF, the Ade1 or Ade2 mutation is complemented only in recombinant cells that contain more than one copy of the ADE1 or ADE2 gene integrated into the genome.

In other embodiments, the integration vectors are provided for the selectable expression of heterologous genes in an expression system employing host cells, which exhibit an Ade1⁻ or Ade2⁻ phenotype, such as the host cells described above. The integration vectors comprise a nucleic acid comprising a promoter sequence and a transcription termination sequence separated by and operably linked to a cloning site. A nucleic acid sequence encoding one or more desired heterologous proteins or peptides or functional nucleic acid of interest is inserted into the cloning site using standard ligation techniques in the proper orientation to be expressed via the promoter. The integration vector preferably comprises at least one promoter, which is functional in the host cell, followed by at least one restriction site, preferably a multiple cloning site, followed by a transcription terminator sequence which is functional in the host cell. Using appropriate known techniques, a nucleotide fragment encoding the desired protein or polypeptide can be ligated into the restriction sites of cloning site of the integration vector. The integration vectors also comprises at least one copy of a selectable marker ORF selected from the group consisting of ADE1 and ADE2, which may be under the control of appropriate transcription termination terminator sequences, which are functional in the host cell. In some embodiments, the ORF is operably linked to a full-strength homologous or heterologous promoter and in other embodiments, the ORF is operably linked to a cryptic promoter, weak promoter, attenuated promoter, or a truncated homologous or heterologous promoter with reduced transcriptional activity compared to the full-strength promoter.

In a further embodiment, provided are methods, materials, and systems for the construction of recombinant host cells for expressing heterologous or recombinant proteins and peptides wherein the ADE1 gene has been removed or deleted to render the host cells auxotrophic for adenine, for example, render the cells ade1. The ade1 host cells are then transformed with an integration vector comprising (1) a nucleic acid encoding the Ade1p or Ade1p activity operably linked to a weak promoter, an attenuated endogenous or heterologous promoter, a cryptic promoter, a truncated endogenous or heterologous promoter, or no promoter; (2) one or more nucleic acids encoding a gene or functional nucleic acid of interest to produce a heterologous or recombinant protein or peptide or functional nucleic acid ectopically; and (3) a targeting nucleic acid sequence that directs insertion of the integration vector into a particular target location or locus of the genome of the host cell by homologous recombination. Stable recombinant host cells in which the integration vector is integrated into the target locus are selected by cultivating the transformed host cells in a culture medium that lacks adenine. Because the nucleic acid encoding the Ade1p activity is operably linked to a weak, attenuated, cryptic promoter, or truncated promoter, the recombinant, transformed host cells containing only one copy of the integration vector inserted into the target locus are not rendered prototrophic for adenine. For the transformed host cells to be rendered prototrophic, multiple copies of the integration vector must be integrated into the target locus for the host cell. In addition, because multiple copies of the integration vector must be integrated into the target locus, significant quantities of the protein or peptide encoded by the gene or sequence of interest are produced.

In another embodiment, provided are methods, materials, and systems for the construction of recombinant host cells for expressing heterologous or recombinant proteins and peptides wherein the ADE2 gene has been removed or deleted to render the host cells auxotrophic for adenine. The ade2 host cells are then transformed with an integration vector comprising (1) a nucleic acid encoding the Ade2p or Ade2p activity operably linked to a weak promoter, an attenuated endogenous or heterologous promoter, a cryptic promoter, a truncated endogenous or heterologous promoter, or no promoter; (2) one or more nucleic acids encoding a gene or functional nucleic acid of interest to produce a heterologous or recombinant protein or peptide or functional nucleic acid ectopically; and (3) a targeting nucleic acid sequence that directs insertion of the integration vector into a particular target location or locus of the genome of the host cell by homologous recombination. Stable recombinant host cells in which the integration vector is integrated into the target locus are selected by cultivating the transformed host cells in a culture medium that lacks adenine. Because the nucleic acid encoding the Ade2p activity is operably linked to a weak, attenuated, or cryptic promoter, the recombinant, transformed host cells containing only one copy of the integration vector inserted into the target locus are not rendered prototrophic for adenine. For the transformed host cells to be rendered prototrophic for adenine, more than one copy of the integration vector must be integrated into the target locus for the host cell. In addition, because multiple copies of the integration vector must be integrated into the target locus, significant quantities of the protein or peptide encoded by the gene or sequence of interest are produced.

In both of the above embodiments, ade1 or ade2 auxotrophs grow more slowly than prototrophs (e.g., ADE1 or ADE2, respectively) or cells rendered prototrophic by integration of multiple copies of the integration vector into the genome. In culture, revertants and transformed cells that lose multiple copies of the integration vector inserted into the target locus will grow more slowly and be out-competed by those cells that maintain the multiple copies of the integration vector integrated into the target locus. In addition, in particular organisms such as yeast, ade1 or ade2 auxotrophs are red or pink in color whereas prototrophs or cells rendered prototrophic by integration of more than one copy of the integration vector into the genome are white. Thus, selection of recombinant cells containing multiple copies of the integration vector inserted into the target sequence can be based upon selecting white colonies.

The methods and systems herein can be practiced in any organism in which auxotrophic mutations can be made such as the ade1 or ade2 and complementation thereof results in the selectable phenotype described herein. The methods involve transforming host cells which exhibit ade1 or ade2 minus phenotype with integration vectors which include nucleotide sequences encoding the complementary Ade1p or Ade2p proteins, such that when the host cells are transformed with the integration vector encoding a desired secreted glycoprotein, the complementation of the Ade1⁻ and/or Ade2⁻ phenotype leads to stable integration of the genes encoding the desired glycoprotein, and contributes to improved quality of the transformed recombinant host cells, particularly, increased yield of the desired recombinant glycoprotein.

In further embodiments, the host cells of the present invention carry other genetic manipulations in their genome, such that the host cells, and/or the proteins or peptides produced therefrom, exhibit desired properties. For example, the host cell may be manipulated in accordance with the methods described in for example, U.S. Pat. No. 7,029,872, U.S. Published Application No. 2004/0018590, and Hamilton et al., Science, 313: 1441-1443 (2006); such that the host cells are capable of producing recombinant glycoproteins with highly homogeneous levels of one or more desired glycoforms. In other embodiments, the host cells may be modified by deleting one or more endogenous genes encoding molecular chaperone proteins and/or transforming the host cell with one or more heterologous genes encoding molecular chaperone genes originating from the species of the heterologous protein or polypeptide to be produced. For example, a host cell of the species *Pichia* may be modified by elimination of the endogenous protein PDI and/or BiP, and transformed with one or ore plasmids encoding mammalian PDI, BiP and/or GRP94 genes. See, Choi et al. supra, the disclosure of which is hereby incorporated herein by reference.

In further still embodiments, methods are provided for increasing the productivity of recombinant human or mammalian glycoproteins in a non-human eukaryotic host cell, lower eukaryotic host cell, or a yeast or filamentous fungal host cell. The methods comprise the step of transforming a host cell, which is ade1 or ade2 and capable of producing glycoproteins having hybrid or complex N-glycans, with a vector comprising a nucleic acid encoding ADE1 or ADE2 ORF and a nucleic acid encoding a glycoprotein of interest.

The following examples are intended to promote a further understanding of the present invention.

Example 1

Cloning of *Pichia pastoris* ADE1 and ADE2 genes was performed as follows.

The cloning of the *P. pastoris* ADE1 gene has been published before (Cereghino et al., supra). Additional 5'- and 3'-sequence was obtained using a partial *P. pastoris* genomic sequence obtained from Integrated Genomics, Chicago, Ill. The nucleotide sequence of the *P. pastoris* ADE1 open reading frame (ORF), including promoter and transcription termination sequences, is shown in SEQ ID NO: 56. The amino acid sequence of the *P. pastoris* ADE1 is shown in SEQ ID NO:57. Querying the same genomic sequence with the *S. cerevisiae* ADE2 ORF, the *P. pastoris* ADE2 homologue (563 amino acids with 69% identity) was identified using the program BLAST (Altschul et al., J. Mol. Biol. 215: 403-410 (1990)). The nucleotide sequence encoding the *P. pastoris* ADE2 ORF, including promoter and transcription termination sequences, is shown in SEQ ID NO:60. The ADE2 ORF is encoded by nucleotides 127 to 1,815 of the nucleotide sequence shown in SEQ ID NO:60 and has the amino acid sequence shown in SEQ ID NO:61. Alignment of the *P. pastoris* ADE2 amino acid sequence (SEQ ID NO:61) to the *S. cerevisiae* ADE2 amino acid sequence (SEQ ID NO:62) is shown in FIG. 1.

Example 2

Construction of ADE1 and ADE2 Knock-Out vectors and strains was as follows. In the first step of plasmid construction, we created a universal knock-out plasmid containing DNA regions of: (a) the ARG3 gene of *P. pastoris* (Nett et al. 2005, supra) as space holders for the 5' and 3' regions of the gene to be knocked out; (b) the *P. pastoris* URA5-blaster (Nett and Gerngross, Yeast 20: 1279-1290 (2003)) as auxotrophic marker; and (c) an expression cassette with a multiple cloning site for insertion of a foreign gene.

To create a URA5-blaster cassette compatible with the architecture of the universal knock-out plasmid the SacI-PvuII fragment of lacZ was cloned into the SacI-SmaI sites of pUC19. The resulting plasmid was digested with HincII and the SacI-PvuII fragment of lacZ that had been blunt-ended using T4DNA polymerase was inserted into this plasmid in a head to tail orientation to yield pGLY8. A 1.0 kb DNA fragment of the *P. pastoris* URA5 gene was amplified using primers Ura5comp5 (SEQ ID NO:1) and Ura5comp3 (SEQ ID NO: 2) and yeast strain NRRL Y-11430 genomic DNA as template and cloned into the BamHI-XbaI sites of pGLY8 to generate pGLY10. In order to remove the internal SacI and XhoI sites three overlapping fragments of URA5 were amplified using pGLY10 as template and primer pairs URA5MUT1 (SEQ ID NO:3) and URA5MUT2 (SEQ ID NO:4), URA5MUT3 (SEQ ID NO:5,) and URA5MUT4 (SEQ ID NO:6), and URA5MUT5 (SEQ ID NO:7) and URA5MUT6 (SEQ ID NO:8) respectively. The resulting PCR products were gel purified, mixed and served as template in a fusion PCR using URA5MUT1 (SEQ ID NO:3) and URA5MUT6 (SEQ ID NO:8) as primers. The resulting PCR product was then cloned into vector pCR2.1 TOPO®, removed again using ClaI and BssHII and cloned into pGLY10 that also had been digested with ClaI and BssHII to yield pGLY12. To remove the SacI and BamHI sites, pGLY12 was first cut with SacI, blunt-ended using T4DNA polymerase and religated creating pGLY13a and then cut with BamHI, blunt-ended and religated to yield pGLY13b. In both cases, the lacZ-URA5 cassette can be released by digestion with EcoRI and SphI.

A 1.1 kb DNA fragment of the ARG3-5' region was amplified by PCR using primers ARG355DIS (SEQ ID NO:9) and ARG353-2 (SEQ ID NO:10) with *P. pastoris* genomic DNA as a template and cloned into the SacI-SalI sites of pUC19. The resulting plasmid was cut with BamHI and SalI and a 0.7 kb DNA fragment of the ARG3-3' region that had been amplified using primers ARG335-2 (SEQ ID NO:11) and ARG333 (SEQ ID NO:12) was cloned into the open sites creating pGLY21. The plasmid was cut with BamHI blunt-ended with T4DNA polymerase and the EcoRI and SphI cut and blunted lacZ-URA5 cassette from pGLY 13a or pGLY13b were inserted resulting in plasmids pGLY22b and pGLY23 respectively. Plasmid pGLY22b constitutes the universal knock-out plasmid without additional expression cassette, whereas pGLY23 was further modified to also contain a cassette for the additional expression of a heterologous gene.

To create an expression cassette with NotI and PacI as cloning sites, a 0.5 kb DNA fragment containing the GAPDH promoter of *P. pastoris* was amplified using primers GAP5CLEAN (SEQ ID NO:13) and GAP3CLEAN (SEQ ID NO:14) and *P. pastoris* genomic DNA as template and cloned into the BamHI-SphI sites of pUC19. The resulting plasmid was cut with SpeI and SphI and a 0.3 kb fragment containing the *S. cerevisiae* CYC1transcriptional terminator region that had been amplified using primers CYC5CLEAN (SEQ ID NO:15) and CYC3CLEAN (SEQ ID NO:16) and *S. cerevisiae* genomic DNA as template and had been cut with NheI and SphI was cloned into the open sites creating pGLY17. The expression cassette was released by BamHI digestion and cloned into pGLY23 to yield pGLY24.

The ADE1 knock-out plasmid was constructed from pGLY22b in the following way. A 1.8 kb fragment of the ADE1-5' region that had been amplified using primers ADE155L (SEQ ID NO:17) and ADE153L (SEQ ID NO:18) was cut with SacI and PmeI and cloned into pGLY22b to yield pGLY1064. Then a 1.5 kb fragment of the ADE1-3' region that had been amplified using primers ADE1KO35 (SEQ ID NO:19) and ADE133L (SEQ ID NO:20) was cut with SwaI and SphI and cloned into pGLY1064 creating the ADE1 knock-out plasmid pGLY1065. (FIG. 1A)

The ADE2 knock-out plasmid was constructed from pGLY24 in the following way. The *P. pastoris* ALG3 transcriptional terminator was PCR amplified using primers RCD534 (SEQ ID NO:21) and RCD535 (SEQ ID NO:22) and *P. pastoris* genomic DNA as template, cut with EcoRV and AflII and cloned into the PmeI-AflII sites of pGLY24 to create pGLY566. This modification is irrelevant for the following ADE2 knock out plasmid, but served to construct a plasmid used for a different project. A 1.7 kb fragment of the ADE2-3' region that had been amplified using primers ADE235 (SEQ ID NO:25) and ADE233 (SEQ ID NO:26) was cut with SwaI and SalI and cloned into pGLY566 to yield pGLY1079. Then a 1.0 kb fragment of the ADE2-5' region that had been amplified using primers ADE255KO (SEQ ID NO:23) and ADE253KO (SEQ ID NO:24) was cut with SacI and FseI and cloned into pGLY1079 to yield the ADE2 knock-out plasmid pGLY2057. (FIG. 1B)

ADE1 and ADE2 knock-out strains were constructed the following way. The strain YGLY24-3 [ura5Δ::MET16, ochlΔ::lacZ, bmt2Δ::lacZ/K1MNN2-2, mnn4L1Δ::lacZ/ MmSLC35A3, pno1Δmnn4Δ::lacZ, met16Δ::lacZ], that had been constructed using methods described earlier (Nett and Gerngross, Yeast 20: 1279-1290 (2003); Choi et al., Proc. Natl. Acad. Sci. 100: 5022-5027 (2003); Hamilton et al., Science 301: 1244-1246 (2003) was transformed with pGLY1065 and two pink transformants were designated YGLY563 and YGLY564. Their Ade1 phenotype was confirmed by their inability to grow on media lacking Adenine. These strains are capable of producing glycoproteins having predominantly Man$_5$GlcNAc$_2$ N-glycans.

Strains YGLY227 and YGLY228 (direct descendants of YGLY24-3 that had been transformed with a URA5 marked *Trichoderma reesei* 1,2 mannosidase expressing plasmid and counterselected on 5-FOA in an unrelated experiment) were transformed with pGLY2057 and for each strain one pink transformant was isolated generating strains YGLY1215 and YGLY1216 respectively. Their ade2 phenotype was also confirmed by their inability to grow on media lacking Adenine (results not shown). As expected (Cereghino et al., supra), both the ade1 and ade2 strains exhibited a slow growth phenotype even on media supplemented with Adenine. These strains are capable of producing glycoproteins having predominantly Man$_5$GlcNAc$_2$ N-glycans.

Example 3

Construction of ADE1 and ADE2 Marked Integration Vectors was as follows.

A vector with a more suitable multiple cloning site containing sites for BglII, EcoRI, KpnI, SwaI, BamHI, NodI, PacI, AscI and SfiI was constructed by cutting pUC19 with EcoRI and HindIII and inserting annealed oligos EXMCS1 (SEQ ID NO:27) and EXMCS2 (SEQ ID NO:28), creating pGLY192. A 0.3 kb DNA fragment containing the *S. cerevisiae* CYC1 transcriptional terminator region that had been amplified using primers CYCTT5 (SEQ ID NO:29) and CYCTT3 (SEQ ID NO:30) and *S. cerevisiae* genomic DNA as template was cut with BamHI and SwaI and cloned into pGLY192 yielding pGLY213. Then the *P. pastoris* AOX1 promoter was amplified from genomic DNA using oligos AOX1P-5 (SEQ ID NO:31) and AOX1P-3 (SEQ ID NO:32), cut with Bgill and EcoRI and ligated into pGLY213 to create pGLY214. Since both ade knock-out plasmids had been designed to remove the complete ORF, a region for integration of the plasmid as an alternative to the promoter region was added. To this end a 1.8 kb fragment containing the *P. pastoris* TRP2 gene was amplified from genomic DNA using oligos TRP2-5 (SEQ ID NO:33) and TRP2-3revised (SEQ ID NO:34), cut with SfiI and cloned into pGLY214 to yield pGLY215. This plasmid contains an EcoRI, KpnI, SwaI site for addition of the gene of interest and a BamHI, NodI, PacI, AscI, site for addition of the truncated ADE markers.

ADE1 marker cassettes containing the ADE1 ORF operably linked to its native promoter or to various truncations of the native promoter were constructed as follows. The ADE1 markers with full-length or truncated promoters were PCR amplified using oligo ADE1-3 (SEQ ID NO:35) as 3'-oligo and ADE1-5C-BAM (SEQ ID NO:36), ADE1-5-100 (SEQ ID NO:37), ADE1-5-186 (SEQ ID NO:38), ADE1-5-295 (SEQ ID NO:39), ADE1-5-325 (SEQ ID NO:40), and ADE1-5ORF (SEQ ID NO:41) as 5'-oligos, yielding fragments with 370, 276, 191, 82, 50, and 0 nucleotides of promoter region respectively. The first five fragments were cut with NotI and AscI and the last fragment was cut with PacI and AscI and all fragments were cloned into pGLY215 to generate the ADE1 marked integration plasmids pGLY220 to pGLY225 respectively (See FIG. 1C for a plasmid map of pGLY225). To create plasmids for constitutive protein expression, the AOX1 promoter in pGLY220 and pGLY225 was removed and replaced by a GAPDH promoter that had been amplified using primers GAPDHP-5 (SEQ ID NO:42) and GAPDHP-3 (SEQ ID NO:43), yielding plasmids pGLY1082 and pGLY1083 respectively (See FIG. 1D for a plasmid map of pGLY1083).

ADE2 marker cassettes containing the ADE2 ORF operably linked to its native promoter or to various truncations of the native promoter were constructed as follows. An unmarked integration plasmid equivalent to pGLY215 for the ADE2 marker cassettes was constructed essentially the same way as above. The main difference between this plasmid, called pGFI4, and pGLY215 was that it contained the GAPDH promoter that had been amplified as above and the multiple cloning site for addition of the gene of interest had been expanded using oligos 5oligoERSSKFS (SEQ ID NO:44) and 3oligoSFSSRF (SEQ ID NO:45) to contain the restriction sites EcoRI, RsrII, SphI, StuI, KpnI, FseI and SwaI. The truncated ADE2 markers were amplified using oligo ADE23 (SEQ ID NO:46) as 3'-oligo and oligos ADE25NotI-1 (SEQ ID NO:47), ADE25NotI-2 (SEQ ID NO:48), ADE25NotI-3 (SEQ ID NO:49), ADE25NotI-4 (SEQ ID NO:50), and ADE25'PacInew (SEQ ID NO:51) as 5'-oligos, yielding fragments with 126, 82, 51, 13, and 0 nucleotides of promoter region respectively. The first four DNA fragments were cut with NotI and AscI and the last DNA fragment was cut with PacI and AscI and all fragments were cloned into pGFI4 to generate the ADE2 marked integration plasmids pGLY2077 to pGLY2081 respectively. In addition to the EcoRI site in the multiple cloning site these plasmids also contain an EcoRI site in the ADE2 ORF.

In pGLY2077 and pGLY2081 the EcoRI site in the ORF was therefore removed by site directed mutagenesis creating pGLY2091 and pGLY2092 respectively. (See FIG. 1E for a plasmid map of pGLY2092). To create plasmids for inducible protein expression, the GAPDH promoter in these two last constructs was removed and replaced by an AOX1 promoter that had been amplified using primers AOX1P-5 (SEQ ID NO:52) and AOX1P-3 (SEQ ID NO:53) as above, yielding plasmids pGLY2093 and pGLY2094 respectively (See FIG. 1F for a plasmid map of pGLY2094).

In order to test the effect of the truncated markers on protein expression, several vectors expressing various proteins of interest were constructed.

Human glucocerebrosidase (GBA) was fused to the human serum albumin (HSA) signal sequence and cloned into the EcoRI/KpnI sites of pGLY1082 and pGLY1083 to create GAPDH driven and ADE1 marked integration vectors pGLY1084 and pGLY1085 respectively. A single-chain version of the anti-HER2 monoclonal antibody Herceptin® (U.S. Patent Application No. 20060252096) fused to the S. cerevisiae alpha mating factor pre-sequence and cloned into the EcoRI/SwaI sites of pGLY1082 and pGLY1083 to yield GAPDH driven and ADE1 marked integration vectors pJN904 and pJN905 respectively. The human CD40 ectodomain (amino acids 20 to 192, a gift of R. J. Noelle; Lu, L. et al., J. Biol. Chem. 278: 45414-45418 (2003) was fused to the S. cerevisiae alpha mating factor prepro-sequence and cloned into the EcoRI/KpnI sites of pGLY 220 and pGLY225 to create AOX1 driven and ADE1 marked integration vectors pGLY1073 and pGLY1074 respectively. Human EPO was fused to the S. cerevisiae alpha mating factor pre-sequence and cloned into the EcoRI/KpnI sites of pGLY2093 and pGLY2094 to yield AOX1 driven and ADE2 marked integration vectors pGLY2663 and pGLY2664 respectively.

Example 4

Effect of ADE marker promoter length on copy number and protein expression was determined.

To test the effect of the various ADE marker promoter truncations on copy number and protein expression, we considered the following assumptions: 1) Since all integration plasmids are integrated into the same genomic locus (TRP2), it is not expected that a reduction of marker promoter strength will lead to an increased copy number of plasmid integrants per se; 2) If the marker promoter strength drops below a certain threshold it is expected that clones integrating only a single copy of the plasmid will grow at a slower rate than clones integrating multiple copies of the plasmid due to the slow growth phenotype of the ade minus phenotype. This should also be concomitant with the appearance of pink color in the low copy clones; 3) A gradual drop in marker promoter strength should therefore lead to decreasing numbers of fast growing white clones and on a relative basis increasing numbers of slow growing pink clones; and, 4) In order to eliminate any effect that the expression of a heterologous protein might exert on the growth of transformants, the empty expression plasmids should be tested initially.

Auxotrophic ade1 strains YGLY563 and YGLY564 were therefore transformed with equal amounts (0.2 µg) of integration plasmids pGLY220 to pGLY225 that had been linearized in the TRP2 integration region using BspEI and spread on minimal media plates. After five days of incubation at 23° C. the transformation plates were assessed for colony number. Surprisingly, integration plasmids pGLY220 to pGLY224 all yielded approximately the same number of colonies. Both yeast strains that had been transformed with pGLY225 however yielded less than 10% of the number of white transformants with a significant number of barely visible, pink transformants in the background (See Table 1). It had been anticipated that the plasmids with the promoter truncations would give rise to smaller number of colonies as the length of the promoter decreased, with the shortest one, only containing the ORF, yielding none. The results however suggest that the CYC1 terminator region and the multiple cloning site in front of the marker contain a cryptic promoter activity that allows for a background level of transcription, thereby resulting in levels of ADE1 gene product that in some cases are enough to complement the ade1 auxotrophic phenotype.

When ade2 auxotrophic strains YGLY1215 and YGLY1216 were transformed with integration plasmids pGLY2077 to pGLY2081, a somewhat similar picture was obtained. In the case of the truncated ADE2 markers however, a gradual reduction in colony number concomitant with a shorter promoter was observed. As was the case for ADE1, the vector only containing the ADE2 ORF with no native promoter sequence at all yielded less than 10% of the number of white transformants than the construct with the full promoter sequence (See Table 1).

TABLE 1

Approximate number of white colonies after transformation of yeast strains with plasmids.

|  | YGLY563 | YGLY564 |
|---|---|---|
| pGLY220 | 300 | 170 |
| pGLY221 | 300 | 170 |
| pGLY222 | 300 | 170 |
| pGLY223 | 300 | 170 |
| pGLY224 | 300 | 170 |
| pGLY225 | 20 | 3 |

|  | YGLY1215 | YGLY1216 |
|---|---|---|
| pGLY2077 | 600 | 600 |
| pGLY2078 | 600 | 500 |
| pGLY2079 | 120 | 80 |
| pGLY2080 | 35 | 40 |
| pGLY2081 | 35 | 25 |

Figure 3A:
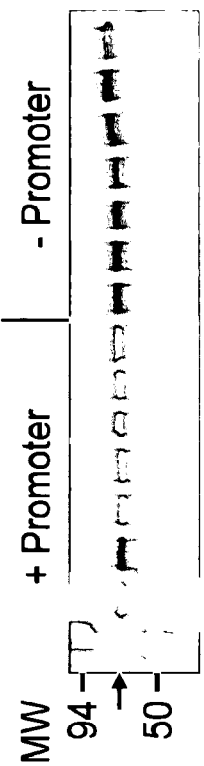
FIG. 3 shows western blots and Coomassie gels of the protein produced in ade1 auxotrophic yeast strains transformed with integration vectors expressing glucocerebrosidase, a single-chain anti-HER2 antibody, or human CD40 ectodomain. Panel A shows the single-chain anti-HER2 antibody produced in seven clones of YGLY563 ade1⁻ cells transformed with pJ903 encoding a single-chain anti-HER2 antibody operably linked to the GAPDH promoter and ADE1 ORF operably linked to its native promoter and the single chain anti-HER2 antibody produced in seven clones of YGLY563 ade1⁻ cells transformed with pJ904 encoding single-chain anti-HER2 antibody operably linked to the GAPDH promoter and ADE1 ORF not operably linked to a promoter. Panel B shows the glucocerebrosidase (GBA) produced in produced in seven clones of YGLY564 ade1⁻ cells transformed with pGly1084 encoding GBA operably linked to the GAPDH promoter and ADE1 ORF operably linked to its native promoter and the GBA produced in seven clones of YGLY564 ade1⁻ cells transformed with pGLY1085 encoding GBA operably linked to the GAPDH promoter and ADE1 ORF not operably linked to a promoter. Panel C shows Coomassie gels of the human CD40 ectodomain produced in six clones of YGLY563 ade1⁻ cells transformed with pGLY1073 encoding human CD40 ectodomain operably linked to the AOX1 promoter and ADE1 ORF operably linked to its native promoter and the human CD40 ectodomain produced in six clones of YGLY563 ade1⁻ cells transformed with pGLY1074 encoding human CD40 ectodomain operably linked to the GAPDH promoter and ADE1 ORF not operably linked to a promoter. Panel D shows the human CD40 ectodomain produced in six clones of YGLY564 ade⁻1 cells transformed with pGLY1073 encoding human CD40 ectodomain operably linked to the AOX1 promoter and ADE1 ORF operably linked to its native promoter and the human CD40 ectodomain produced in six clones of YGLY564 ade⁻ cells transformed with pGLY1074 encoding human CD40 ectodomain operably linked to the AOX1 promoter and ADE1 ORF not operably linked to a promoter.
Figure 3B:
Figure 3C:
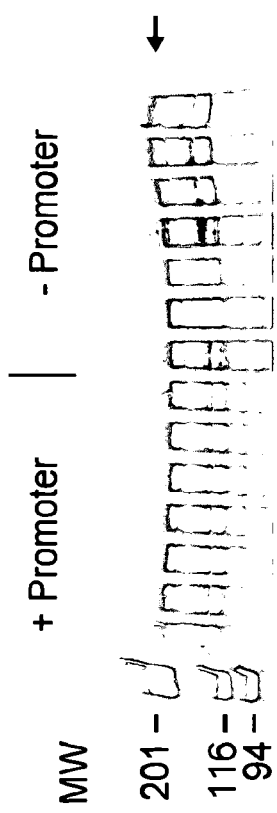
Figure 3D:
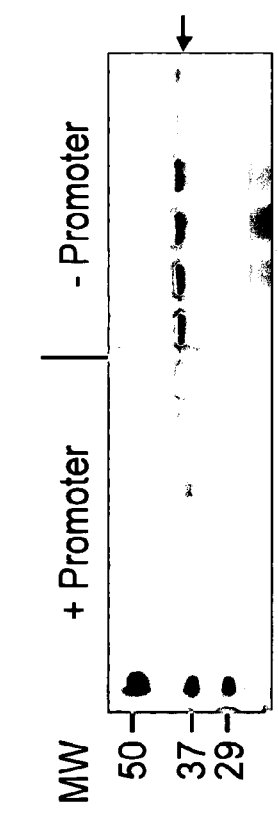
Figure 4A:
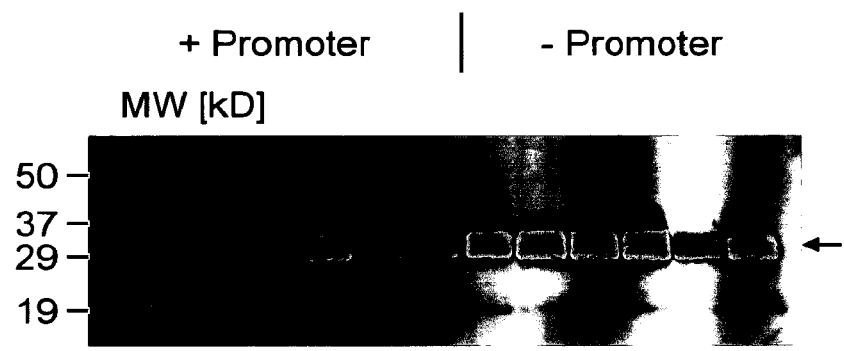
FIG. 4 shows western blots of the protein produced in ade2 auxotrophic yeast strains transformed with integration vectors encoding erythropoietin (EPO). Panel A shows the EPO produced in six clones of YGLY1215 ade2⁻ cells transformed with pGly2663 encoding EPO operably linked to the AOX1 promoter and ADE1 ORF operably linked to its native promoter and the EPO produced in six clones of YGLY1215 ade2-cells transformed with pGly2664 encoding EPO operably linked to the AOX1 promoter and ADE2 ORF not operably linked to a promoter. Panel B shows the EPO produced in six clones of YGLY1216 ade2⁻ cells transformed with pGly2663 encoding EPO operably linked to the AOX1 promoter and ADE1 ORF operably linked to its native promoter and the EPO produced in six clones of YGLY1216 ade2⁻ cells transformed with pGly2664 encoding EPO operably linked to the AOX1 promoter and ADE2 ORF not operably linked to a promoter.
Figure 4B:
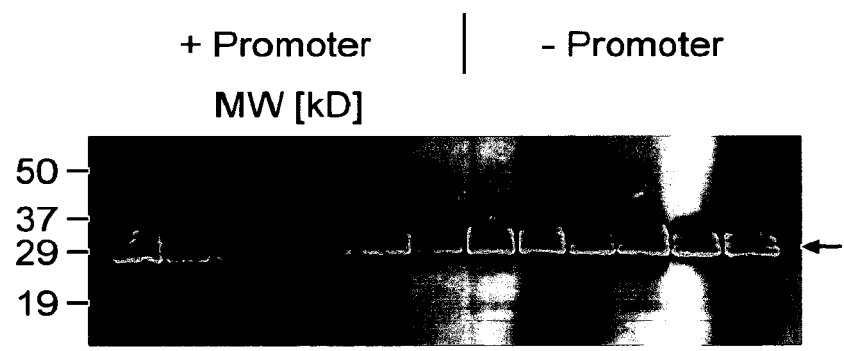

In order to test how this anticipated multicopy integration affected protein expression levels, plasmids expressing GBA, single-chain anti-HER2 antibody, human CD40 ectodomain or human EPO were transformed into ade1 or ade2 auxotrophic yeast strains (See Table 2). Transformants were grown in 96 well deep well plates, expression was induced using the appropriate carbon source and protein levels were assessed by Western Blot or Coomassie gel (See FIGS. 3 and 4). For most transformations using the promoterless ADE2 ORF as marker, as expected, a very low number of white transformants (5 to 20) were observed. However the expression level of those clones was generally significantly higher than clones obtained from transformations using the complete ADE2 gene as marker, which usually gave rise to hundreds of transformants (See FIGS. 3 and 4). Especially striking is the amount of protein produced from the clone shown in the lane marked in FIG. 3D with an asterisk.

TABLE 2

Transformation of yeast strains with plasmids expressing heterologous proteins.

| Yeast Strain | Plasmid | Auxotrophic Marker | Protein Expressed | Promoter | FIG. |
|---|---|---|---|---|---|
| YGLY563 | pJN903 | ADE1 + promoter | single chain anti-HER2 antibody | GAPDH | 3A |
| YGLY563 | pJN904 | ADE1 – promoter | single chain anti-HER2 antibody | GAPDH | 3A |
| YGLY564 | pGLY1084 | ADE1 + promoter | Glucocerebrosidase | GAPDH | 3B |
| YGLY564 | pGLY1085 | ADE1 – promoter | Glucocerebrosidase | GAPDH | 3B |
| YGLY563 | pGLY1073 | ADE1 + promoter | Human CD40 Ectodomain | AOX1 | 3C |
| YGLY563 | pGLY1074 | ADE1 – promoter | Human CD40 Ectodomain | AOX1 | 3C |
| YGLY564 | pGLY1073 | ADE1 + promoter | Human CD40 Ectodomain | AOX1 | 3D |
| YGLY564 | pGLY1074 | ADE1 – promoter | Human CD40 Ectodomain | AOX1 | 3D |
| YGLY1215 | pGLY2663 | ADE2 + promoter | Human EPO | AOX1 | 4A |
| YGLY1215 | pGLY2664 | ADE2 – promoter | Human EPO | AOX1 | 4A |
| YGLY1216 | pGLY2663 | ADE2 + promoter | Human EPO | AOX1 | 4B |
| YGLY1216 | pGLY2664 | ADE2 – promoter | Human EPO | AOX1 | 4B |

Materials and Methods

*Escherichia coli* strain DH5a was used for recombinant DNA work. Wild type *P. pastoris* strain NRRL-Y 11430 was used for construction of yeast strains (ATCC #76273). PCR reactions were performed according to supplier recommendations using EXTAQ (TaKaRa), Taq Poly (Promega) or Pfu Turbo® (Stratagene, La Jolla, Calif.). Restriction and modification enzymes were from New England Biolabs (Beverly, Mass.). Yeast strains were grown in YPD (1% yeast extract, 2% peptone, 2% dextrose and 1.5% agar) or synthetic defined medium (1.4% yeast nitrogen base, 2% dextrose, $4\times10^{-5}$% biotin and 1.5% agar) supplemented as appropriate. Yeast transformations were performed by electroporation as described in (Nett et al., 2005). Coomassie gels and Western Blots were performed using 4-20% precast TRIS-SDS gels and the Mini PROTEAN 3 cell from Biorad according to the manufacturer's instructions. Primary antibodies for detection were: Goat Anti-Human IgG (Fc) #31413 from Pierce at 1:10000 dilution for Herceptin; Anti human EPO #sc7956 from Santa Cruz Biotechnology at 1:500 dilution; Anti-GBA rabbit polyclonal (custom made) from Rockland Immunochemicals, Inc. at 1:500 dilution.

While the present invention is described herein with reference to illustrated embodiments, it should be understood that the invention is not limited hereto. Those having ordinary skill in the art and access to the teachings herein will recognize additional modifications and embodiments within the scope thereof. Therefore, the present invention is limited only by the claims attached herein.

BRIEF DESCRIPTION OF THE SEQUENCES

| SEQ ID NO: | Name | Sequence (5' to 3') |
|---|---|---|
| 1 | Ura5comp5 | GCTCTAGAGGGACTTATCTGGGTCCAGACGATGTG |
| 2 | Ura5comp3 | CGGGATCCGCCGCCGTGCCCAAAGCTCCGAAACAG |
| 3 | URA5MUT1 | GCAGTCATCACATCATCGATAATCAGTACTC |
| 4 | URA5MUT2 | CCGTGTTGAAGTTGTACGAGCTGGGCGGC |
| 5 | URA5MUT3 | GCCGCCCAGCTCGTACAACTTCAACACGG |
| 6 | URA5MUT4 | CACATTGAAGATGTCACTGGAGGGGTACC |
| 7 | URA5MUT5 | GGTACCCCTCCAGTGACATCTTCAATGTG |
| 8 | URA5MUT6 | GCTGGCTCGCGCGCAGTGTTTTCGTGCTC |
| 9 | ARG355DIS | GAGCTCGGCCAGCTTGGCCGCTAACAGTAACAAAAACTACCGCCAG |
| 10 | ARG353-2 | GTCGACGGATCCGTTTAAACGACAGCCTTCTTTGGGTCATGAGTAACTTCCAAAC |
| 11 | ARG335-2 | GGATCCACTAGTATTTAAATCACGGATTTATGCTTGATCACATGACCAATCATAAC |
| 12 | ARG333 | GTCGACGGCCGATGGGGCCCGCATTCTTCTTGCTTAATAAACC |
| 13 | GAP5CLEAN | GGATCCCTCGAGAGATCTTTTTTGTAGAAATGTCTTGGTGTCCTCGTC |

| SEQ ID NO: | Name | Sequence (5' to 3') |
|---|---|---|
| 14 | GAP3CLEAN | GCATGCACTAGTGCGGCCGCTGTGTTTTGATAGTTGTTCAATTGATTGAAATAG |
| 15 | CYC5CLEAN | GCTAGCTTAATTAAACAGGCCCCTTTTCCTTTGTCGATATCATG |
| 16 | CYC3CLEAN | GCATGCGGATCCCTTAAGAGCCGGCAGCTTGCAAATTAAAGCCTTCGAGCGTCC |
| 17 | ADE155L | CCACCGAGCTCGGCCAACTCGGCCTTTTCAAGTTGATGCTATCTTTTATGGATATTAAGCCAG |
| 18 | ADE153L | CCACCGTTTAAACCTCCATGCCACCCATCTAATGTTGATCAACG |
| 19 | ADE1KO35 | ATTTAAATATGATTAGTACCCTCCTCGCCTTTTTTCAGAC |
| 20 | ADE133L | CCACCGCATGCGGCCATGTTGGCCCCTCTTTAAGCAACTCTCTTGGTCCTTGG |
| 21 | RCD534 | GATATCGGCCGGCCATTTACAATTAGTAATATTAAGGTGG |
| 22 | RCD535 | CTTAAGCGGACCGGTTTAAACCTACTAAGCGACGAAAACGGGAGC |
| 23 | ADE255KO | GGATGAGCTCGGCCAGTTGGGCCCTTAAAATCATCTGCCTCACCCCACCGACC |
| 24 | ADE253KO | GGATGGCCGGCCGACTTGCTAACCTGGCTCTGCCATAGTTGAAAATACGTCG |
| 25 | ADE235 | GGACGATTTAAATATTTAGTATTGTTTTTAATAGATGTATATATAATAGTACACG |
| 26 | ADE233 | GGACGGTCGACGGCCATACTGGCCTGAGATGGATTTGAAATGCTC |
| 27 | EXMCS1 | AATTGAGATCTGAATTCGGTACCATTTAAATGGATCCGCGGCCGCTTAATTAAGGCGCGCCAGGCCATAATGGCCT |
| 28 | EXMCS2 | AGCTAGGCCATTATGGCCTGGCGCGCCTTAATTAAGCGGCCGCGGATCCATTTAAATGGTACCGAATTCAGATCTC |
| 29 | CYCTT5 | GCAAGGATTTAAATACAGGCCCCTTTTCCTTTGTCGATATCATG |
| 30 | CYCTT3 | GGATCCAGCTTGCAAATTAAAGCCTTCGAGCGTCC |
| 31 | AOX1P-5 | AGATCTAACATCCAAAGACGAAAGGTTGAATGAAACC |
| 32 | AOX1P-3 | GAATTCCGTTTCGAATAATTAGTTGTTTTTTGATCTTC |
| 33 | TRP2-5 | GGCCATAATGGCCAAACGGTTTCTCAATTACTATATACTACTAAC |
| 34 | TRP2-3 revised | GGCCATTATGGCCAAACCATAAATTCCTACTTACGTCCTCCG |
| 35 | ADE1-3 | GGCGCGCCCTGAGCCAAAAGACCCCCTGCCAATGAGC |
| 36 | ADE1-5C-BAM | GCGGCCGCGGGTGCTATCGTTTTGTGCAATTGGTTTGC |
| 37 | ADE1-5-100 | GCGGCCGCACTTTTACCAATAATCGTTTATGAATACGG |
| 38 | ADE1-5-186 | GCGGCCGCTCCACTTGAACGATTCATTATTCAGA |
| 39 | ADE1-5-295 | GCGGCCGCCCAATATACTACTCTAGGAAACTCGAAAAAC |
| 40 | ADE1-5-325 | GCGGCCGCCCCTTTCCATGTGTCATCGCTTCCAACACAC |
| 41 | ADE1-5-ORF | TTAATTAAATGTCCATTGTGAACACTGATCTGGACGGAA |
| 42 | GAPDHP-5 | AGATCTTTTTTGTAGAAATGTCTTGGTGTCCTCGTCC |
| 43 | GAPDHP-3 | GAATTCTGTGTTTTGATAGTTGTTCAATTGATTG |
| 44 | 5oligo ERSSKFS | AATTCCGGACCGGCATGCAGGCCTGGTACCGGCCGGCCATTT |
| 45 | 3oligoSFSSRF | AAATGGCCGGCCGGTACCAGGCCTGCATGCCGGTCCGG |
| 46 | ADE23AscI | GGATGGCGCGCCGCACATGAGGCTCTTTGCAAAGTTCCTCCAGG |
| 47 | ADE25NotI-1 | GGATGCGGCCGCGTCAAAGCCGTATACTCGGTAGTGTGCTCGCC |
| 48 | ADE25NotI-2 | GGATGCGGCCGCGACTTGACTCTTCACTAGCCTATGCAAATAAGG |
| 49 | ADE25NotI-3 | GGATGCGGCCGCGGTTACCTTTTCCAAGAATCGTAGAAACGATT |
| 50 | ADE25NotI-4 | GGATGCGGCCGCCTTCCAAACTCTCATGGATTCTCAGGTAATAG |
| 51 | ADE2-5'PacInew | GGCCTTAATTAAATGGATTCTCAGGTAATAGGTATTCTAGGAGGAGGCCAGCTAGGCCG |
| 52 | AOX1P-5 | AGATCTAACATCCAAAGACGAAAGGTTGAATGAAACC |
| 53 | AOX1P-3 | GAATTCCGTTTCGAATAATTAGTTGTTTTTTGATCTTC |
| 54 | ADE 1 5' seq for KO | TTTTTCAAGTTGATGCTATCTTTTATGGATATTAAGCCAGTGAAACTTAGAGTTAGCAGTATCTTATCAAGAGTGAAAAAGTTGTGTTTCTTTTCATTTGAATTGTGCTTGGTCATTGATGAAATCAGAGTCATTCTCAAGATGTATAACCATATCGATCTATAAGTCGCAGTTGCTTCCAAGTTGACTCTTGCTCAATATCCAGATCTATGGAATCTTGAGCAGGTCTTTTGGAATAAAATGCGACTAAAAACCCAGAAAGTAGCCCAATTATATGCAGTCTGAACATGAGTGGTACTTTGGTGAGTGACCTCCATATCCATGACATGGATGGATTTCGCCCTTTTCTTGTGTAATATGACATCAACAACGACGTGGATGACACAGTAACAACAGTCAAGGAGAGTTTGAGACTTTCTTTTACGCTTTTTATGACTATCTGTTTGTAATACTTCCATTTGCTAGCCGCTTTCAGCTGTTCCAATTCTTCCGTGCTAAGTCTCAAGTTCATAAAGAAGAAAATGGAAAGAGGTATTCAAGGACTACCGTGTATTTTCTTGGCAAATATCGCAACAGAAAGTTTCTAGATCAAATGCAAATCGATTTTTCATGCTATTCTTACCAATTATGCTTTCCAGTTCATAGAAAGATTTGACCATATCACCAGATGAAACCATGCGAGAAGTTCCTCTTTTGACTAATAGGCCTTCACCCATAAAGTTTAAGATGTTCCTGAAATATACTGGACAGTTCTCGTAATCCATGATAAACGACTTGAAAATCTGCGAGTAACATAATGGGAA |

| SEQ ID NO: | Name | Sequence (5' to 3') |
|---|---|---|
| | | TAGATACCATGAACGTAAGAGTTTGTCTCTC<br>TTTGGAACACTTTTTAGCGCTTTGAGCCTAC<br>GAATGAAACAACTATTTTCTGGTTGATCTTC<br>GAATTCAGCGTTGTCTGTGTCTTTCATATCA<br>GAATCCTTGATAACGTATATAGAGGATGTCT<br>CTTTGGAAAATTGGTCGGGGTAAACCTGTTC<br>CAAGAACTTATAGCCATACTCTACCATTAAT<br>ACCGTAAAATATATTGATGCATAATTCTTTT<br>GGTAATATATTTTACTGGGATACAGGGCAAA<br>TGACACCACTGATGTGAATAGACTGGAAACG<br>ACTGAATTGAAAAGAAACTTTTGCTTCTCAG<br>TGACTTTTAAATAGCTCTCTGCGAAAATGTC<br>AAGAATCTTGTTGAACAATGGTTTAACTGAA<br>AATAAGAGAGCCCAGTGATGTAGAAAATTTTA<br>GCAAATTCACCCGATCATTGAACATTAAATT<br>TCTTCTAGAATTTGCAATATTCAACTTTCTT<br>AAGATCTTAAATATTACGCCCAACGATCCAA<br>ACAACAATAGAAACCATCTGTTGAAGTTTCT<br>AGCTGCCTTTATGGTGACTTTTAGTATTCCT<br>GTTGTGTCGTTCTCATAAAATGACTGTTCTA<br>CAGTCGATAATAAGCCACTCATCTTCCACAA<br>CTTCAACTGCACTTCCTCCAATGCAACTAGA<br>TCATGCTTTTCAAGCTGCTTGAGATTGATCT<br>TCAGTAATTCTTTAACTTCATCGTGTGATGT<br>GAGCAAGACGAGTAAATACTTGAGTTTTGTC<br>AAGTTATTACTGCCCTTGTTTGACATGGATT<br>GCTGTATTTGAGAAGAAAAATGAACGTAAAC<br>TTGAATCTCCCCAGGTGAACTTGGCGTGTAT<br>CTTATCTACCCCAGCTCTAAAGTTTACCCGA<br>TGAGGTAATTCTTAGGGATAATTTGGTGTAT<br>GGATTTGACTAAATTGCCGGAGTTGATTCAA<br>TGACAGAGAAGCTTACATGCAAGGAACATGA<br>TTCGTTGATCAACATTAGATGGGTGGCATGG<br>AG |
| 55 | ADE 1 3' seq, for KO | ATGATTAGTACCCTCCTCGCCTTTTTCAGAC<br>ATCTGAAATTTCCCTTATTCTTCCAATTCCA<br>TATAAAATCCTATTTAGGTAATTAGTAAACA<br>ATGATCATAAAGTGAAATCATTCAAGTAACC<br>ATTCCGTTTATCGTTGATTTAAAATCAATAA<br>CGAATGAATGTCGGTCTGAGTAGTCAATTTG<br>TTGCCTTGGAGCTCATTGGCAGGGGGTCTTT<br>TGGCTCAGTATGGAAGGTTGAAAGGAAAACA<br>GATGGAAAGTGGTTCGTCAGAAAAGAGGTAT<br>CCTACATGAAGATGAATGCCAAAGAGATATC<br>TCAAGTGATAGCTGAGTTCAGAATTCTTAGT<br>GAGTTAAGCCATCCCAACATTGTGAAGTACC<br>TTCATCACGAACATATTTCTGAGAATAAAAC<br>TGTCAATTTATACATGGAATACTGTGATGGT<br>GGAGATCTCTCCAAGCTGATTCGAACACATA<br>GAAGGAACAAAGAGTACATTTCAGAGAAAA<br>AATATGGAGTATTTTTACGCAGGTTTTATTA<br>GCATTGTATCGTTGTCATTATGGAACTGATT<br>TCACGGCTTCAAAGGAGTTTGAATCGCTCAA<br>TAAAGGTAATAGACGAACCCAGAATCCTTCG<br>TGGGTAGACTCGACAAGAGTTATTATTCACA<br>GGGATATAAAACCCGACAACATCTTTCTGAT<br>GAACAATTCAAACCTTGTCAAACTGGGAGAT<br>TTTGGATTAGCACAAAATTCTGGACCAAGAA<br>ACGATTTTGCCAAAACATACGTCGGTACGCC<br>GTATTACATGTCTCCTGAAGTGCTGTTGGAC<br>CAACCCTACTCACCATTATGTGATATATGGT<br>CTCTTGGGTGCGTCATGTATGAGCTATGTGC<br>ATTGCAGGTCTCCTTTTCAAGCCACTACACAT<br>TTACAATTACAACAAAAGATCAAGAAGGGA<br>CATTCCCTCCACTTCCGGACGTATTTTCACC<br>CCGGTTAAGATCTCTGATCAATGCTTGCATA<br>ACCATAGACCTGAACCAACGACCATCTACTC<br>ACGACTTCTTCAGGAAAGTTGCTTCAATGT<br>GTATATCAAGGAGGTTAATTTAGAGATAAGG<br>GAGGACAGATTGAATGAGCGTGAACGCAAAC<br>TGAAAATACGAGAGAACAAGTTAATCTTGAG<br>CGAAGAGGGAATAGTGAAACAACTGAATGAA<br>GAACTGGAATTTCAAAGAAAGTTGCTTGAAC<br>AAGAAGTAGAGGAAATAAGGAAGTCATACAA |
| | | GAACGAATTTCAGTTCGTACTGGAACAACAG<br>GTGCAACAGGCATTGAGCAAAATTCTAGGTC<br>CCCAATACAATCAAAAGCCATTGAACAGGAA<br>TCAGCAACAAAAACAAATACAACAAATTTAC<br>AGCAGACAGGATCCGCAATTATCAAGCCCAA<br>AGTCACAACAAGCTCAGATCCAAGGACCAAG<br>AGAGTTGCTTAAAAGAGG |
| 56 | ADE1 gene (including promoter and terminator) | GGGTGCTATCGTTTTGTGCAATTTGGTTTGC<br>TGGAGAGTCGACCAAGAGATGATAACTGTTA<br>CTAAGCTTCTCCGTAATTAGTGGTATTTTGT<br>AACTTTTACCAATAATCGTTTATGAATACGG<br>ATATTTTTCGACCTTATCCAGTGCCAAATCA<br>CGTAACTTAATCATGGTTTAAATACTCCACT<br>TGAACGATTCATTATTCAGAAAAAAGTCAGG<br>TTGGCAGAAACACTTGGGCGCTTTGAAGAGT<br>ATAAGAGTATTAAGCATTAAACATCTGAACT<br>TTCACCGCCCCAATATACTACTCTAGGAAAC<br>TCGAAAAATTCCTTTCCATGTGTCATCGCTT<br>CCAACACACTTTGCTGTATCCTTCCAAGTAT<br>GTCCATTGTGAACACTGATCTGGACGGAATC<br>CTACCTTTAATCGCCAAAGGAAAGGTTAGAG<br>ACATTATGCAGTCGATGAGAACAACTTGCT<br>GTTCGTCGCAACTGACCGTATCTCCGCTTAC<br>GATGTGATTATGACAAACGGTATTCCTGATA<br>AGGGAAAGATTTTGACTCAGCTCTCAGTTTT<br>CTGGTTTGATTTTTTGGCACCCTACATAAAG<br>AATCATTTGGTTGCTTCTAATGACAAGGAAG<br>TCTTTGCTTTACTACCATCAAAACTGTCTGA<br>AGAAAAATACAAATCTCAATTAGAGGGACGA<br>TCCTTGATAGTAAAAAAGCACAGACTGATAC<br>CTTTGGAAGCCATTGTCAGAGGTTACATCAC<br>TGGAAGTGCATGGAAAGAGTACAAGAACTCA<br>AAAACTGTCCATGGAGTCAAGGTTGAAAACG<br>AGAACCTTCAAGAGAGCGACGCCTTTCCAAC<br>TCCGATTTTCACACCTTCAACGAAAGCTGAA<br>CAGGGTGAACACGATGAAAACATCTCTATTG<br>AACAAGCTGCTGAGATTGTAGGTAAAGACAT<br>TTGTGAGAAGGTCGCTGTCAAGGCGGTCGAG<br>TTGTATTCTGCTGCAAAAAACTTCGCCCTTT<br>TGAAGGGGATCATTATTGCTGATACGAAATT<br>CGAATTTGGACTGGACGAAAACAATGAATTG<br>GTACTAGTAGATGAAGTTTTAACTCCAGATT<br>CTTCTAGATTTTGGAATCAAAAGACTTACCA<br>AGTGGGTAAATCGCAAGAGAGTTACGATAAG<br>CAGTTTCTCAGAGATTGGTTGACGGCCAACG<br>GATTGAATGGCAAAGAGGGCGTGGCCATGGA<br>TGCAGAAATTGCTATCAAGAGTAAAGAAAAG<br>TATATTGAAGCTTATGAAGCAATTACTGGCA<br>AGAAATGGCTTGATGATTAGTACCCTCCT<br>CGCCTTTTTCAGACATCTGAAATTTCCCTTA<br>TTCTTCCAATTCCATATAAAATCCTATTTAG<br>GTAATTAGTAAACAATGATCATAAAGTGAAA<br>TCATTCAAGTAACCATTCCGTTTATCGTTGA<br>TTTAAAATCAATAACGAATGAATGTCGGTCT<br>GAGTAGTCAATTTGTTGCCTTGGAGCTCATT<br>GGCAGGGGGTCTTTTGGCTCAG |
| 57 | ADE1 aa seq | MSIVNTDLDGILPLIAKGKVRDIYAVDENNL<br>LFVATDRISAYDVIMTNGIPDKGKILTQLSV<br>FWFDFLAPYIKNHLVASNDKEVFALLPSKLS<br>EEKYKSQLEGRSLIVKKHRLIPLEAIVRGYI<br>TGSAWKEYKNSKTVHGVKVENENLQESDAFP<br>TPIFTPSTKAEQGEHDENISIEQAAEIVGKD<br>ICEKVAVKAVELYSAAKNFALLKGIIIADTK<br>FEFGLDENNELVLVDEVLTPDSSRFWNQKTY<br>QVGKSQESYDKQFLRDWLTANGLNGKEGVAM<br>DAEIAIKSKEKYIEAYEAITGKKWA |
| 58 | ADE 2 5' seq for KO | AGTTGGGCCCTTAAAATCATCTGCCTCACCC<br>CACCGACCAATGGGAATTCTAGAAACAATTT<br>CATTGCTCTTCTTCTCGTTACCATAAGAATC<br>GGCTGTCATGTTTGACTTAACGAACCCTGGA<br>ACAAGGGAATTCACGGTAATACCTTTTGGAG<br>CAAGTTCAACCGATAGAGCCTTCATTAATGA |

| SEQ ID NO: | Name | Sequence (5' to 3') |
|---|---|---|
| | | GTTGATTGCACCTTTGGTGGTCGCATATACC GATTGATTCGGGTAGGTCACTTCGAAACTGT ACAGGGAGGCAGTAAAGATGATCCTACCCTT AATCTGGTTCTTAATAAAGTGTTTAGTGACT AGCTGTGTCAATCTAAATGGAAAATCGACAT TTACCTTTTGGATAGCCGCGTAATCTTTCTC CGTAAAACTTGTAAACTCAGATTTAATGGCA ATGGCAGCGTTGTTGATTAAAATGTCAATCT TTCCAGTGGAACTCTTCTTCCACCGCAGGACT CGTTACGGTCTCTTCCAGCTTTGCAAGATCG GCATCCACTAGATCCAACTCAATTGTATGTA TGGAGGCACCATCGGCATTTGACATTCTCAC CTCTTCAATGAAAGCCGTTGGGTCTGTAGAA GGTCTATGGATAAGAATAAGTTCTGCACCTG CTTCATAAAGTCCTCGAACTATTCCTTGGCC TAATCCGCTGGTACCACCGGTGATCAAGGCG ACCTTACCATTCAAAGAAAACAAATCAGCGG ACATTAGCGACTTGATAGGGAATGGGTTAG ACAAATGAAAGCCGACGAGCCAGCACTTTAT AGTAAGTGCAGGTGAGTCAATAAGAATAAAT GTATGGCTTGCTGTCCCTATCGCGTAAGAAG CTTACTAAGATCGCCTAAATTGAAAAGTTGA ACAAATCAGTTCTAGCTGGCCTCCATCAGCA TTTCGTTCTCCTCTGATCATCTTTGCCAATC GCTAGCATGCCCTCAGCGTGCAAGGAAAAGC ACGCTTCTTTCTTATCGACGTATTTTCAACT ATGGCAGAGCCAGGTTAGCAAGTC |
| 59 | ADE 2 3' seq, for KO | ATTTAGTATTGTTTTTTAATAGATGTATATA TAATAGTACACGTAACTTATCTATTCCATTC ATAATTTTATTTTAAAGGTTCGGTAGAAATT TGTCCTCCAAAAGTTGGTTAGAGCCTGGCA GTTTTGATAGGCATTATTATAGATTGGGTAA TATTTACCCTGCACCTGGAGGAACTTTGCAA AGAGCCTCATGTGCTCTAAAAGGATGTCAGA ATTCCAACATTTCAAAATTATATCTGCATGC GTCTGTAATACTGGAACTGTTATTTTTCTGG TCAGGATTTCACCGCTCTTGTCGTCATGTTT CTCGTCGTCTGAAAGTAAACTGACTTTCCTC TTTCCATAAACACAAAAATCGATTGCAACTT GGTTATTCTTGAGATTGAAATTTGCTGTGTC TTCAGTGCTTAGCTGAATATCAACAAACTTA CTTAGTACTAATAACGAAGCACTATGGTAAG TGGCATAACATAGTGGTATTGAAGCGAACAG TGGATATTGAACCCAAGCATTGGCAACATCT GGCTCTGTTGATACTGATCCGGATCGTTTGG CACCAATTCCTGAAACGGCGTAGTGCCACCA AGGTTTCGATTTGAGAACAGGTTCATCATCA GAGTCAACCACCCCAATGTCAATGGCAGGCT CCAACGAAGTAGGTCCAACAACAACAGGAAG TATTTGACCTTGAAGATCTGTTCCTTTATGA TCCACCACACCTTGCCCCAATTCCAATAACT TTACCAGTCCCGATGCAGACATGATAACTGG TACTAATGATCTCCATTGATTTTCGTCGGCA CTACGTAAAGCCTCCAAAAATGAATTCAGAA TATCTTCTGAAACTAGATTCTGCTTCTGTGA TTCAAGCATTGCTTTATGTAGACATCTCTTG AATAAAAGCAATTCTCCACATATTGGTGTGT GTAAGATAGATCTGGAAAGATGTATCTGGAA TAGTCCAGTCAACGTTGTGCAATTGATTAGC ATTACCTTACTGTGAACATCTCTATCTACAA CAACAGACTCAATTCGATAGACGTTCCGGGA AGTTTTTCAAGCGCATTCAGTTTGCTGTTG AACAAGTGACTTTGCTTTCCAATGTGCAAA TACCCCTGTATATCAAGTCCATCACATCACT CAAGACCTTGGTGAAAAGAATGAAACAGCT GGAGCATAATTTTCGAATGAATTAGGTAAGG TCACTTCATCCTTATCTGTTGTAATGCTATA ATCAATAGCGGAACTAACATCTTTCCCATGT ACAGGTTTCTTGATCTCTGAATCTGAATCTT TATTTGAAAAAGAATTGAAAAAGACTCATC ACTCATTGGGAATTCAAGGTCATTAGGGTAT TCCATTGTTAGTTCTGGTCTAGGTTTAAAGG GATCACCTTCGTTAAGACGATGGAAAATAGC TAATCTGTACAATAACCAGATACTTCTAACG |
| | | AAGCTCTCTCTATCCATCAGTTGACGTGTTG AGGATATCTGAACTAGCTCTTTCCACTGCGA ATCAGGCATGCTCGTATAGCTGGCAAGCATG TTATTCAGCTTTACCAAGTTAGAAGCCCTTT GGAAACCATCTATAGATTCCCGAAAAAACTT ATACCCACTGAGGGTTTCACTGAGCATAGTC AGTGACATCAAAGAGCATTTCAAATCCATCT CA |
| 60 | ADE2 gene (including promoter and terminator) | GTCAAAGCCGTATACTCGGTAGTGTGCTCGC CAAAAATAAATTTGACTTGACTCTTCACTAG CCTATGCAAATAAGGTTACCTTTTCCAAGAA TCGTAGAAACGATTAAAAAACTTCCAAACTC TCATGGATTCTCAGGTAATAGGTATTCTAGG AGGAGGCCAGCTAGGCCGAATGATTGTTGAG GCCGCTAGCAGGCTCAATATCAAGACCGTGA TTCTTGATGATGGTTTTTCACCTGCTAAGCA CATTAATGCTGCGCAAGACCACATCGACGGA TCATTCAAAGATGAGGAGGCTATCGCCAAGT TAGCTGCCAAATGTGATGTTCTCACTGTAGA GATTGAGCATGTCAACACAGATGCTCTAAAG AGAGTTCAAGACAGAACTGGAATCAAGATAT ATCCTTTACCAGAGACAATCGAACTAATCAA GGATAAGTACTTGCAAAAGGAACATTTGATC AAGCACAACATTTCGGTGACAAAGTCTCAGG GTATAGAATCTAATGAAAAGGCGCTGCTTTT GTTTGGAGAAGAATGGATTTCCATATCTG TTGAAGTCCCGGACTATGCTTATGATGGAA GAGGCAATTTTGTAGTGGAGTCTAAAGAGGA CATCGTAAGGCATTAGAATTCTTGAAAGAT CGTCCATTGTATGCCGAGAAGTTTGCTCCTT TTGTTAAAGAATTAGCGGTAATGGTTGTGAG ATCACTGGAAGGCGAAGTATTCTCCTACCCA ACCGTAGAAACTGTGCACAAGGACAATATCT GTCATATTGTGTATGCTCCGGCCAGAGTTAA TGACACCATCCAAAAGAAAGCTCAAATATTA GCTGAAAACACTGTGAAGACTTTCCCAGGCG CTGGAATCTTCGGAGTTGAGATGTTCCTATT GTCTGATGGAGAACTTCTTGTAAATGAGATT GCTCCAAGGCCCCACAATTCTGGTCACTATA CAATCGATGCATGTGTAACATCTCAGTTCGA AGCACATGTAAGAGCCATAACTGGTCTGCCA ATGCCACTAGATTTCACCAAACTATCTACTT CCAACACCAACGCTATTATGCTCAATGTTTT GGGTGCTGAAAAATCTCACGGGGAATTAGAG TTTTGTAGAAGAGCCTTAGAAACACCCGGTG CTTCTGTATATCTGTACGGAAAGACCACCCG ATTGGCTCGTAAGATGGGTCATATCAACATA ATAGGATCTTCCATGTTGGAAGCAGAACAAA AGTTAGAGTACATTCTAGAAGAATCAACCCA CTTACCATCCAGTACTGTTATCAGCTGACACT AAACCGTTGGTTGGAGTTATCATGGGTTCAG ACTCTGATCTACCTGTGATTTCGAAAGGTTG CGATATTTTAAAACAGTTTGGTGTTCCATTC GAAGTTACTATTGTCTCTGCTCATAGAACAC CACAGAGAATGACCAGATATGCCTTTGAAGC CGCTAGTAGAGGTATCAAGGCTATCATTGCA GGTGCTGGTGGTGCTGCTCATCTTCCAGGAA TGGTTGCTGCCATGACTCCGTTGCCAGTCAT TGGTGTTCCTGTCAAGGGCTCTACGTTGGAT GGTGTAGACTCGCTACACTCGATTGTCCAAA TGCCTAGAGGTGTTCCTGTGGCTACGGTTGC TATCAACAACGCCACCAATGCCGCTCTGTTG GCCATCAGGATTTTAGGTACAATTGACCACA AATGGCAAAAGGAAATGTCCAAGTATATGAA TGCAATGGAGACCGAAGTGTTGGGGAAGGCA TCCAACTTGGAATCTGAAGGGTATGAATCCT ATTTGAAGAATCGTCTTTGAATTTAGTATTG TTTTTAATAGATGTATATAATAGTACAC GTAACTTATCTATTCCATTCATAATTTTATT TTAAAGGTTCGGTAGAAATTGTCCTCCAAA AAGTTGGTTAGAGCCTGGCAGTTTTGATAGG CATTATTATAGATTGGGTAATATTTACCCTG CACCTGGAGGAACTTTGCAAAGAGCCTCATG TGC |

| SEQ ID NO: | Name | Sequence (5' to 3') |
|---|---|---|
| 61 | ADE2 aa seq | MDSQVIGILGGGQLGRMIVEAASRLNIKTVI LDDGFSPAKHINAAQDHIDGSFKDEEAIAKL AAKCDVLTVEIEHVNTDALKRVQDRTGIKIY PLPETIELIKDKYLQKEHLIKHNISVTKSQG IESNEKALLLFGEENGFPYLLKSRTMAYDGR GNFVVESKEDISKALEFLKDRPLYAEKFAPF VKELAVMVVRSLEGEVFSYPTVETVHKDNIC HIVYAPARVNDTIQKKAQILAENTVKTFPGA GIFGVEMFLLSDGELLVNEIAPRPHNSGHYT IDACVTSQFEAHVRAITGLPMPLDFTKLSTS NTNAIMLNVLGAEKSHGELEFCRRALETPGA SVYLYGKTTRLARKMGHINIIGSSMLEAEQK LEYILEESTHLPSSTVSADTKPLVGVIMGSD SDLPVISKGCDILKQFGVPPFEVTIVSAHRTP QRMTRYAFEAASRGIKAIIAGAGGAAHLPGM VAAMTPLPVIGVPVKGSTLDGVDSLHSIVQM PRGVPVATVAINNATNAALLAIRILGTIDHK WQKEMSKYMNAMETEVLGKASNLESEGYESY LKNRL |
| 62 | S.c. ADE2 aa seq | MDSRTVGILGGGQLGRMIVEAANRLNIKTVI LDAENSPAKQISNSNDHVNGSFSNPLDIEKL AEKCDVLTIEIEHVDVPTLKNLQVKHPKLKI YPSPETIRLIQDKYIQKEHLIKNGIAVTQSV PVEQASETSLLNVGRDLGFPFVLKSRTLAYD GRGNFVVKNKEMIPEALEVLKDRPLYAEKWA PFTKELAVMIVRSVNGLVFSYPIVETIHKDN ICDLCYAPARVPDSVQLKAKLLAENAIKSFP GCGIFGVEMFYLETGELLINEIAPRPHNSGH YTIDACVTSQFEAHLRSILDLPMPKNFTSFS TITTNAIMLNVLGDKHTKDKELETCERALAT PGSSVYLYGKESRPNRKVGHINIIASSMAEC EQRLNYITGRTDIPIKISVAQKLDLEAMVKP LVGIIMGSDSDLPVMSAACAVLKDFGVPFEV TIVSAHRTPHRMSAYAISASKRGIKTIIAGA GGAAHLPGMVAAMTPLPVIGVPVKGSCLDGV DSLHSIVQMPRGVPVATVAINNSTNAALLAV RLLGAYDSSYTTKMEQFLLKQEEEVLVKAQK LETVGYEAYLENK |

What is claimed:

1. A method for expressing a recombinant peptide, proteins, and/or nucleic acid of interest in a lower eukaryote host cell comprising:
    (a) providing the host cell in which the endogenous ADE2 gene has been removed from the genome of the host cell; and
    (b) transforming the host cell with an integration vector comprising:
        (1) a nucleic acid having an open reading frame (ORF) encoding Ade2p and which is operably linked to
            (i) a truncated endogenous ADE2 promoter that consists of 3' 51 nucleotides or less,
            (ii) a truncated endogenous ADE2 promoter that consists of 3' 13 nucleotides or less, or
            (iii) no promoter;
        (2) a nucleic acid having one or more expression cassettes comprising a nucleic acid encoding a peptide, polypeptide, protein, or functional nucleic acid of interest, wherein the functional nucleic acid is selected from the group consisting of ribozyme, antisense nucleic acid, and siRNA molecule; and
        (3) a targeting nucleic acid that directs insertion of the integration vector into a particular location of the genome of the host cell by homologous recombination, wherein the transformed host cell produces the recombinant peptide, protein and/or nucleic acid of interest.

2. The method of claim 1, wherein the recombinant vector comprises multiple insertion sites for the insertion of one or more expression cassettes encoding the one or more heterologous peptides or proteins.

3. The method of claim 1, wherein the recombinant vector comprises more than one expression cassette.

4. The method of claim 3, wherein the recombinant vector comprises little or no homologous DNA sequence between the expression cassettes.

5. The method of claim 3, wherein the recombinant vector comprises a first expression cassette encoding a light chain of a monoclonal antibody and a second expression cassette encoding a heavy chain of a monoclonal antibody.

6. The method of claim 1, wherein the host cell is from a species selected from the group consisting of *Pichia pastoris, Pichia finlandica, Pichia trehalophila, Pichia koclamae, Pichia membranaefaciens, Pichia minuta, Ogataea minuta, Pichia lindneri, Pichia opuntiae, Pichia thermotolerans, Pichia salictaria, Pichia guercuum, Pichia pijperi, Pichia stiptis, Pichia methanolica, Pichia* sp., *Saccharomyces cerevisiae, Saccharomyces* sp., *Hansenula polymorpha, Kluyveromyces* sp., *Kluyveromyces lactis, Candida albicans, Aspergillus nidulans, Aspergillus niger, Aspergillus oryzae, Trichoderma reesei, Chrysosporium lucknowense, Fusarium* sp., *Fusarium gramineum, Fusarium venenatum, Physcomitrella patens*, and *Neurospora crassa*.

7. The method of claim 1, wherein the host cell is *Pichia pastoris*.

8. The method of claim 7, wherein the *Pichia pastoris* cell has been modified to be capable of producing glycoproteins having hybrid or complex N-glycans.

9. The method of claim 1, wherein the truncated endogenous ADE2 promoter consists of 3 51 nucleotides or less.

* * * * *

SEQUENCE LISTING

<160> NUMBER OF SEQ ID NOS: 62

<210> SEQ ID NO 1
<211> LENGTH: 35
<212> TYPE: DNA
<213> ORGANISM: Artificial Sequence
<220> FEATURE:
<223> OTHER INFORMATION: Ura5comp5 primer

<400> SEQUENCE: 1
gctctagagg gacttatctg ggtccagacg atgtg                       35

<210> SEQ ID NO 2
<211> LENGTH: 35
<212> TYPE: DNA
<213> ORGANISM: Artificial Sequence
<220> FEATURE:
<223> OTHER INFORMATION: Ura5comp3 primer

<400> SEQUENCE: 2
cgggatccgc cgccgtgccc aaagctccga aacag                       35

<210> SEQ ID NO 3
<211> LENGTH: 31
<212> TYPE: DNA
<213> ORGANISM: Artificial Sequence
<220> FEATURE:
<223> OTHER INFORMATION: URA5MUT1 primer

<400> SEQUENCE: 3
gcagtcatca catcatcgat aatcagtact c                           31

<210> SEQ ID NO 4
<211> LENGTH: 29
<212> TYPE: DNA
<213> ORGANISM: Artificial Sequence
<220> FEATURE:
<223> OTHER INFORMATION: URA5MUT2 primer

<400> SEQUENCE: 4
ccgtgttgaa gttgtacgag ctgggcggc                              29

<210> SEQ ID NO 5
<211> LENGTH: 29
<212> TYPE: DNA
<213> ORGANISM: Artificial Sequence
<220> FEATURE:
<223> OTHER INFORMATION: URA5MUT3 primer

<400> SEQUENCE: 5
gccgcccagc tcgtacaact tcaacacgg 29

<210> SEQ ID NO 6
<211> LENGTH: 29
<212> TYPE: DNA
<213> ORGANISM: Artificial Sequence
<220> FEATURE:
<223> OTHER INFORMATION: URA5MUT4 primer

<400> SEQUENCE: 6
cacattgaag atgtcactgg aggggtacc 29

<210> SEQ ID NO 7
<211> LENGTH: 29
<212> TYPE: DNA
<213> ORGANISM: Artificial Sequence
<220> FEATURE:
<223> OTHER INFORMATION: URA5MUT5 primer

<400> SEQUENCE: 7
ggtacccctc cagtgacatc ttcaatgtg 29

<210> SEQ ID NO 8
<211> LENGTH: 30
<212> TYPE: DNA
<213> ORGANISM: Artificial Sequence
<220> FEATURE:
<223> OTHER INFORMATION: URA5MUT6 primer

<400> SEQUENCE: 8
gctggctcgc gcgcagtgtt tttcgtgctc 30

<210> SEQ ID NO 9
<211> LENGTH: 46
<212> TYPE: DNA
<213> ORGANISM: Artificial Sequence
<220> FEATURE:
<223> OTHER INFORMATION: ARG355DIS primer

<400> SEQUENCE: 9
gagctcggcc agcttggccg ctaacagtaa caaaaactac cgccag 46

<210> SEQ ID NO 10
<211> LENGTH: 55
<212> TYPE: DNA
<213> ORGANISM: Artificial Sequence
<220> FEATURE:
<223> OTHER INFORMATION: ARG353-2 primer

<400> SEQUENCE: 10
gtcgacggat ccgtttaaac gacagccttc tttgggtcat gagtaacttc caaac 55

<210> SEQ ID NO 11
<211> LENGTH: 56
<212> TYPE: DNA
<213> ORGANISM: Artificial Sequence
<220> FEATURE:

<223> OTHER INFORMATION: ARG335-2 primer

<400> SEQUENCE: 11
ggatccacta gtatttaaat cacggattta tgcttgatca catgaccaat cataac    56

<210> SEQ ID NO 12
<211> LENGTH: 43
<212> TYPE: DNA
<213> ORGANISM: Artificial Sequence
<220> FEATURE:
<223> OTHER INFORMATION: ARG333 primer

<400> SEQUENCE: 12
gtcgacggcc gatggggccc gcattcttct tgcttaataa acc    43

<210> SEQ ID NO 13
<211> LENGTH: 48
<212> TYPE: DNA
<213> ORGANISM: Artificial Sequence
<220> FEATURE:
<223> OTHER INFORMATION: GAP5CLEAN primer

<400> SEQUENCE: 13
ggatccctcg agagatcttt tttgtagaaa tgtcttggtg tcctcgtc    48

<210> SEQ ID NO 14
<211> LENGTH: 54
<212> TYPE: DNA
<213> ORGANISM: Artificial Sequence
<220> FEATURE:
<223> OTHER INFORMATION: GAP3CLEAN primer

<400> SEQUENCE: 14
gcatgcacta gtgcggccgc tgtgttttga tagttgttca attgattgaa atag    54

<210> SEQ ID NO 15
<211> LENGTH: 44
<212> TYPE: DNA
<213> ORGANISM: Artificial Sequence
<220> FEATURE:
<223> OTHER INFORMATION: CYC5CLEAN primer

<400> SEQUENCE: 15
gctagcttaa ttaaacaggc ccctttcct ttgtcgatat catg    44

<210> SEQ ID NO 16
<211> LENGTH: 54
<212> TYPE: DNA
<213> ORGANISM: Artificial Sequence
<220> FEATURE:
<223> OTHER INFORMATION: CYC3CLEAN primer

<400> SEQUENCE: 16
gcatgcggat cccttaagag ccggcagctt gcaaattaaa gccttcgagc gtcc    54

<210> SEQ ID NO 17
<211> LENGTH: 64
<212> TYPE: DNA
<213> ORGANISM: Artificial Sequence
<220> FEATURE:
<223> OTHER INFORMATION: ADE155L primer

<400> SEQUENCE: 17
ccaccgagct cggccaactc ggcctttttc aagttgatgc tatctttat ggatattaag    60 ccag    64

<210> SEQ ID NO 18
<211> LENGTH: 44
<212> TYPE: DNA
<213> ORGANISM: Artificial Sequence
<220> FEATURE:
<223> OTHER INFORMATION: ADE153L primer

<400> SEQUENCE: 18
ccaccgttta aacctccatg ccacccatct aatgttgatc aacg         44

<210> SEQ ID NO 19
<211> LENGTH: 39
<212> TYPE: DNA
<213> ORGANISM: Artificial Sequence
<220> FEATURE:
<223> OTHER INFORMATION: ADE1KO35 primer

<400> SEQUENCE: 19
atttaaatat gattagtacc ctcctcgcct ttttcagac              39

<210> SEQ ID NO 20
<211> LENGTH: 54
<212> TYPE: DNA
<213> ORGANISM: Artificial Sequence
<220> FEATURE:
<223> OTHER INFORMATION: ADE133L primer

<400> SEQUENCE: 20
ccaccgcatg cggccatgtt ggcccctctt ttaagcaact ctcttggtcc ttgg    54

<210> SEQ ID NO 21
<211> LENGTH: 40
<212> TYPE: DNA
<213> ORGANISM: Artificial Sequence
<220> FEATURE:
<223> OTHER INFORMATION: RCD534 primer

<400> SEQUENCE: 21
gatatcggcc ggccatttac aattagtaat attaaggtgg              40

<210> SEQ ID NO 22
<211> LENGTH: 45
<212> TYPE: DNA
<213> ORGANISM: Artificial Sequence
<220> FEATURE:
<223> OTHER INFORMATION: RCD535 primer

<400> SEQUENCE: 22
cttaagcgga ccggtttaaa cctactaagc gacgaaaacg ggagc         45

<210> SEQ ID NO 23
<211> LENGTH: 53
<212> TYPE: DNA
<213> ORGANISM: Artificial Sequence
<220> FEATURE:
<223> OTHER INFORMATION: ADE255KO primer

<400> SEQUENCE: 23
ggatgagctc ggccagttgg gcccttaaaa tcatctgcct caccccaccg acc    53

<210> SEQ ID NO 24
<211> LENGTH: 52
<212> TYPE: DNA
<213> ORGANISM: Artificial Sequence
<220> FEATURE:

<223> OTHER INFORMATION: ADE253KO primer

<400> SEQUENCE: 24
ggatggccgg ccgacttgct aacctggctc tgccatagtt gaaaatacgt cg     52

<210> SEQ ID NO 25
<211> LENGTH: 56
<212> TYPE: DNA
<213> ORGANISM: Artificial Sequence
<220> FEATURE:
<223> OTHER INFORMATION: ADE235 primer

<400> SEQUENCE: 25
ggacgattta aatatttagt attgtttttt aatagatgta tataatag tacacg     56

<210> SEQ ID NO 26
<211> LENGTH: 45
<212> TYPE: DNA
<213> ORGANISM: Artificial Sequence
<220> FEATURE:
<223> OTHER INFORMATION: ADE233 primer

<400> SEQUENCE: 26
ggacggtcga cggccatact ggcctgagat ggatttgaaa tgctc     45

<210> SEQ ID NO 27
<211> LENGTH: 76
<212> TYPE: DNA
<213> ORGANISM: Artificial Sequence
<220> FEATURE:
<223> OTHER INFORMATION: EXMCS1 primer

<400> SEQUENCE: 27
aattgagatc tgaattcggt accatttaaa tggatccgcg gccgcttaat taaggcgcgc     60
caggccataa tggcct     76

<210> SEQ ID NO 28
<211> LENGTH: 76
<212> TYPE: DNA
<213> ORGANISM: Artificial Sequence
<220> FEATURE:
<223> OTHER INFORMATION: EXMCS2 primer

<400> SEQUENCE: 28
agctaggcca ttatggcctg gcgcgcctta attaagcggc cgcggatcca tttaaatggt     60
accgaattca gatctc     76

<210> SEQ ID NO 29
<211> LENGTH: 44
<212> TYPE: DNA
<213> ORGANISM: Artificial Sequence
<220> FEATURE:
<223> OTHER INFORMATION: CYCTT5 primer

<400> SEQUENCE: 29
gcaaggattt aaatacaggc ccctttttcct ttgtcgatat catg     44

<210> SEQ ID NO 30
<211> LENGTH: 35
<212> TYPE: DNA
<213> ORGANISM: Artificial Sequence
<220> FEATURE:
<223> OTHER INFORMATION: CYCTT3 primer

<400> SEQUENCE: 30

```
ggatccagct tgcaaattaa agccttcgag cgtcc                                35
```

<210> SEQ ID NO 31
<211> LENGTH: 37
<212> TYPE: DNA
<213> ORGANISM: Artificial Sequence
<220> FEATURE:
<223> OTHER INFORMATION: AOX1P-5 primer

<400> SEQUENCE: 31

```
agatctaaca tccaaagacg aaaggttgaa tgaaacc                              37
```

<210> SEQ ID NO 32
<211> LENGTH: 38
<212> TYPE: DNA
<213> ORGANISM: Artificial Sequence
<220> FEATURE:
<223> OTHER INFORMATION: AOX1P-3 primer

<400> SEQUENCE: 32

```
gaattccgtt tcgaataatt agttgttttt tgatcttc                             38
```

<210> SEQ ID NO 33
<211> LENGTH: 45
<212> TYPE: DNA
<213> ORGANISM: Artificial Sequence
<220> FEATURE:
<223> OTHER INFORMATION: TRP2-5 primer

<400> SEQUENCE: 33

```
ggccataatg gccaaacggt ttctcaatta ctatatacta ctaac                     45
```

<210> SEQ ID NO 34
<211> LENGTH: 42
<212> TYPE: DNA
<213> ORGANISM: Artificial Sequence
<220> FEATURE:
<223> OTHER INFORMATION: TRP2-3revised primer

<400> SEQUENCE: 34

```
ggccattatg gccaaaccat aaattcctac ttacgtcctc cg                        42
```

<210> SEQ ID NO 35
<211> LENGTH: 37
<212> TYPE: DNA
<213> ORGANISM: Artificial Sequence
<220> FEATURE:
<223> OTHER INFORMATION: ADE1-3 primer

<400> SEQUENCE: 35

```
ggcgcgccct gagccaaaag accccctgcc aatgagc                              37
```

<210> SEQ ID NO 36
<211> LENGTH: 39
<212> TYPE: DNA
<213> ORGANISM: Artificial Sequence
<220> FEATURE:
<223> OTHER INFORMATION: ADE1-5C-BAM primer

<400> SEQUENCE: 36

```
gcggccgcgg gtgctatcgt tttgtgcaat ttggtttgc                            39
```

<210> SEQ ID NO 37
<211> LENGTH: 38
<212> TYPE: DNA

<213> ORGANISM: Artificial Sequence
<220> FEATURE:
<223> OTHER INFORMATION: ADE1-5-100 primer

<400> SEQUENCE: 37
gcggccgcac ttttaccaat aatcgtttat gaatacgg        38

<210> SEQ ID NO 38
<211> LENGTH: 34
<212> TYPE: DNA
<213> ORGANISM: Artificial Sequence
<220> FEATURE:
<223> OTHER INFORMATION: ADE1-5-186 primer

<400> SEQUENCE: 38
gcggccgctc cacttgaacg attcattatt caga        34

<210> SEQ ID NO 39
<211> LENGTH: 39
<212> TYPE: DNA
<213> ORGANISM: Artificial Sequence
<220> FEATURE:
<223> OTHER INFORMATION: ADE1-5-295 primer

<400> SEQUENCE: 39
gcggccgccc aatatactac tctaggaaac tcgaaaaac        39

<210> SEQ ID NO 40
<211> LENGTH: 38
<212> TYPE: DNA
<213> ORGANISM: Artificial Sequence
<220> FEATURE:
<223> OTHER INFORMATION: ADE1-5-325 primer

<400> SEQUENCE: 40
gcggccgccc tttccatgtg tcatcgcttc caacacac        38

<210> SEQ ID NO 41
<211> LENGTH: 39
<212> TYPE: DNA
<213> ORGANISM: Artificial Sequence
<220> FEATURE:
<223> OTHER INFORMATION: ADE1-5-ORF primer

<400> SEQUENCE: 41
ttaattaaat gtccattgtg aacactgatc tggacggaa        39

<210> SEQ ID NO 42
<211> LENGTH: 37
<212> TYPE: DNA
<213> ORGANISM: Artificial Sequence
<220> FEATURE:
<223> OTHER INFORMATION: GAPDHP-5 primer

<400> SEQUENCE: 42 agatctttt tgtagaaatg tcttggtgtc ctcgtcc        37

<210> SEQ ID NO 43
<211> LENGTH: 34
<212> TYPE: DNA
<213> ORGANISM: Artificial Sequence
<220> FEATURE:
<223> OTHER INFORMATION: GAPDHP-3 primer

<400> SEQUENCE: 43
gaattctgtg ttttgatagt tgttcaattg attg        34

<210> SEQ ID NO 44
<211> LENGTH: 42
<212> TYPE: DNA
<213> ORGANISM: Artificial Sequence
<220> FEATURE:
<223> OTHER INFORMATION: 5oligoERSSKFS primer

<400> SEQUENCE: 44
aattccggac cggcatgcag gcctggtacc ggccggccat tt                    42

<210> SEQ ID NO 45
<211> LENGTH: 38
<212> TYPE: DNA
<213> ORGANISM: Artificial Sequence
<220> FEATURE:
<223> OTHER INFORMATION: 3oligoSFSSRF primer

<400> SEQUENCE: 45
aaatggccgg ccggtaccag gcctgcatgc cggtccgg                         38

<210> SEQ ID NO 46
<211> LENGTH: 44
<212> TYPE: DNA
<213> ORGANISM: Artificial Sequence
<220> FEATURE:
<223> OTHER INFORMATION: ADE23AscI primer

<400> SEQUENCE: 46
ggatggcgcg ccgcacatga ggctctttgc aaagttcctc cagg                  44

<210> SEQ ID NO 47
<211> LENGTH: 44
<212> TYPE: DNA
<213> ORGANISM: Artificial Sequence
<220> FEATURE:
<223> OTHER INFORMATION: ADE25NotI-1 primer

<400> SEQUENCE: 47
ggatgcggcc gcgtcaaagc cgtatactcg gtagtgtgct cgcc                  44

<210> SEQ ID NO 48
<211> LENGTH: 45
<212> TYPE: DNA
<213> ORGANISM: Artificial Sequence
<220> FEATURE:
<223> OTHER INFORMATION: ADE25NotI-2 primer

<400> SEQUENCE: 48
ggatgcggcc gcgacttgac tcttcactag cctatgcaaa taagg                 45

<210> SEQ ID NO 49
<211> LENGTH: 44
<212> TYPE: DNA
<213> ORGANISM: Artificial Sequence
<220> FEATURE:
<223> OTHER INFORMATION: ADE25NotI-3 primer

<400> SEQUENCE: 49
ggatgcggcc gcggttacct tttccaagaa tcgtagaaac gatt                  44

<210> SEQ ID NO 50
<211> LENGTH: 44
<212> TYPE: DNA
<213> ORGANISM: Artificial Sequence
<220> FEATURE:

<223> OTHER INFORMATION: ADE25NotI-4 primer

<400> SEQUENCE: 50
ggatgcggcc gccttccaaa ctctcatgga ttctcaggta atag                44

<210> SEQ ID NO 51
<211> LENGTH: 59
<212> TYPE: DNA
<213> ORGANISM: Artificial Sequence
<220> FEATURE:
<223> OTHER INFORMATION: ADE2-5'PacInew primer

<400> SEQUENCE: 51
ggccttaatt aaatggattc tcaggtaata ggtattctag gaggaggcca gctaggccg    59

<210> SEQ ID NO 52
<211> LENGTH: 37
<212> TYPE: DNA
<213> ORGANISM: Artificial Sequence
<220> FEATURE:
<223> OTHER INFORMATION: AOX1P-5 primer

<400> SEQUENCE: 52
agatctaaca tccaaagacg aaaggttgaa tgaaacc                          37

<210> SEQ ID NO 53
<211> LENGTH: 38
<212> TYPE: DNA
<213> ORGANISM: Artificial Sequence
<220> FEATURE:
<223> OTHER INFORMATION: AOX1P-3 primer

<400> SEQUENCE: 53
gaattccgtt tcgaataatt agttgttttt tgatcttc                         38

<210> SEQ ID NO 54
<211> LENGTH: 1831
<212> TYPE: DNA
<213> ORGANISM: Artificial Sequence
<220> FEATURE:
<223> OTHER INFORMATION: ADE 1 5' seq for Knockout

<400> SEQUENCE: 54
tttttcaagt tgatgctatc ttttatggat attaagccag tgaaacttag agttagcagt    60
atcttatcaa gagtgaaaaa gttgtgtttc ttttcatttg aattgtgctt ggtcattgat   120
gaaatcagag tcattctcaa gatgtataac catatcgatc tataagtcgc agttgcttcc   180
aagtttgact cttgctcaat atccagatct atggaatctt gagcaggtct tttggaataa   240
aatgcgacta aaacccagaa agtagcccca attatatgca gtctgaacat gagtgggtact  300 ttggtgagtg acctccatat ccatgacatg gatggatttc gcccttttct tgtgtaatat   360
gacatcaaca acgacgtgga tgacacagta acaacagtca aggagagttt gagactttct   420
tttacgcttt ttatgactat ctgtttgtaa tacttccatt tgctagccgc tttcagctgt   480
tccaattctt ccgtgctaag tctcaagttc ataagaaga aaaatggaaa gaggtattca    540
aggactaccg tgtattttct tggcaaatat cgcaacagaa agtttctcag atcaaatgca   600 atcgatttt tcatgctatt cttaccaatt atgctttcca gttcatagaa agatttgacc    660
atatcaccag atgaaaccat gcgagaagtt cctctttga ctaataggcc ttcacccata    720
aagtttaaga tgttcctgaa atatactgga cagttctcgt aatccatgat aaacgacttg   780
aaaatctgcg agtaacataa tgggaataga taccatgaac gtaagagttt gtctctcttt   840

```
ggaacacttt ttagcgcttt gagcctacga atgaaacaac tattttctgg ttgatcttcg      900
aattcagcgt tgtctgtgtc tttcatatca gaatccttga taacgtatat agaggatgtc      960
tctttggaaa attggtcggg gtaaacctgt tccaagaact tatagccata ctctaccatt     1020
aataccgtaa aatatattga tgcataattc ttttggtaat atattttact gggatacagg     1080
gcaaatgaca ccactgatgt gaatagactg gaaacgactg aattgaaaag aaacttttgc     1140
ttctcagtga cttttaaata gctctctgcg aaaatgtcaa gaatcttgtt gaacaatggt     1200
ttaactgaaa ataagagacc cagtgatgta gaaaatttta gcaaattcac ccgatcattg     1260
aacattaaat ttcttctaga atttgcaata ttcaactttc ttaagatctt aaatattacg     1320
cccaacgatc caaacaacaa tagaaaccat ctgttgaagt ttctagctgc ctttatggtg     1380
acttttagta ttcctgttgt gtcgttctca taaaatgact gttctacagt cgataataag     1440
ccactcatct tccacaactt caactgcact cctccaatg caactagatc atgctttca      1500 agctgcttga gattgatctt cagtaattct ttaacttcat cgtgtgatgt gagcaagacg     1560
agtaaatact tgagttttgt caagttatta ctgcccttgt ttgacatgga ttgctgtatt     1620
tgagaagaaa aatgaacgta aacttgaatc tccccaggtg aacttggcgt gtatcttatc     1680
taccccagct ctaaagttta cccgatgagg taattcttag ggataatttg gtgtatggat     1740
ttgactaaat tgccggagtt gattcaatga cagagaagct tacatgcaag gaacatgatt     1800
cgttgatcaa cattagatgg gtggcatgga g                                    1831

<210> SEQ ID NO 55
<211> LENGTH: 1444
<212> TYPE: DNA
<213> ORGANISM: Artificial Sequence
<220> FEATURE:
<223> OTHER INFORMATION: ADE 1 3' seq for  Knockout

<400> SEQUENCE: 55
atgattagta ccctcctcgc cttttttcaga catctgaaat ttcccttatt cttccaattc       60
catataaaat cctatttagg taattagtaa acaatgatca taaagtgaaa tcattcaagt      120
aaccattccg tttatcgttg atttaaaatc aataacgaat gaatgtcggt ctgagtagtc      180
aatttgttgc cttggagctc attggcaggg ggtcttttgg ctcagtatgg aaggttgaaa      240
ggaaaacaga tggaaagtgg ttcgtcagaa aagaggtatc ctacatgaag atgaatgcca      300
aagagatatc tcaagtgata gctgagttca gaattcttag tgagttaagc catcccaaca      360
ttgtgaagta ccttcatcac gaacatattt ctgagaataa aactgtcaat ttatacatgg      420
aatactgtga tggtggagat ctctccaagc tgattcgaac acatagaagg aacaaagagt      480
acatttcaga agaaaaaata tggagtattt ttacgcaggt tttattagca ttgtatcgtt      540
gtcattatgg aactgatttc acggcttcaa aggagtttga atcgctcaat aaaggtaata      600
gacgaaccca gaatccttcg tgggtagact cgacaagagt tattattcac agggatataa      660
aacccgacaa catctttctg atgaacaatt caaaccttgt caaactggga gattttggat      720
tagcaaaaat tctggaccaa gaaaacgatt ttgccaaaac atacgtcggt acgccgtatt      780
acatgtctcc tgaagtgctg ttggaccaac cctactcacc attatgtgat atatggtctc      840
ttgggtgcgt catgtatgag ctatgtgcat tgaggcctcc ttttcaagcc actacacatt      900
tacaattaca acaaaagatc caagaaggga cattccctcc acttccggac gtattttcac      960
cccggttaag atctctgatc aatgcttgca taaccataga cctgaaccaa cgaccatcta     1020
```

```
ctcacgaact tcttcaggaa agttgcttca atgtgtatat caaggaggtt aatttagaga    1080
taagggagga cagattgaat gagcgtgaac gcaaactgaa aatacgagag aacaagttaa    1140
tcttgagcga agagggaata gtgaaacaac tgaatgaaga actggaattt caaagaaagt    1200
tgcttgaaca agaagtagag gaaataagga agtcatacaa gaacgaattt cagttcgtac    1260
tggaacaaca ggtgcaacag gcattgagca aaattctagg tccccaatac aatcaaaagc    1320
cattgaacag gaatcagcaa caaaaacaaa tacaacaaat ttacagcaga caggatccgc    1380
aattatcaag cccaaagtca caacaagctc agatccaagg accaagagag ttgcttaaaa    1440
gagg                                                                1444

<210> SEQ ID NO 56
<211> LENGTH: 1510
<212> TYPE: DNA
<213> ORGANISM: Pichia pastoris

<400> SEQUENCE: 56
gggtgctatc gttttgtgca atttggtttg ctggagagtc gaccaagaga tgataactgt      60
tactaagctt ctccgtaatt agtggtattt tgtaactttt accaataatc gtttatgaat     120
acggatattt ttcgacctta tccagtgcca aatcacgtaa cttaatcatg gtttaaatac     180
tccacttgaa cgattcatta ttcagaaaaa agtcaggttg cagaaacac ttgggcgctt      240 tgaagagtat aagagtatta agcattaaac atctgaactt tcaccgcccc aatatactac     300
tctaggaaac tcgaaaaatt cctttccatg tgtcatcgct tccaacacac tttgctgtat     360
ccttccaagt atgtccattg tgaacactga tctggacgga atcctacctt taatcgccaa     420
aggaaaggtt agagacattt atgcagtcga tgagaacaac ttgctgttcg tcgcaactga     480
ccgtatctcc gcttacgatg tgattatgac aaacggtatt cctgataagg aaagattttt     540
gactcagctc tcagtttttct ggtttgattt tttggcaccc tacataaaga atcatttggt     600
tgcttctaat gacaaggaag tctttgcttt actaccatca aaactgtctg aagaaaaata     660
caaatctcaa ttagagggac gatccttgat agtaaaaaag cacagactga taccttggga     720
agccattgtc agaggttaca tcactggaag tgcatggaaa gagtacaaga actcaaaaac     780
tgtccatgga gtcaaggttg aaaacgagaa ccttcaagag agcgacgcct tccaactcc      840 gatttcaca ccttcaacga aagctgaaca gggtgaacac gatgaaaaca tctctattga     900
acaagctgct gagattgtag gtaaagacat tgtgagaag gtcgctgtca aggcggtcga      960
gttgtattct gctgcaaaaa acttcgccct tttgaagggg atcattattg ctgatacgaa    1020
attcgaattt ggactggacg aaaacaatga attggtacta gtagatgaag ttttaactcc    1080
agattcttct agattttgga atcaaaagac ttaccaagtg ggtaaatcgc aagagagtta    1140
cgataagcag tttctcagag attggttgac ggccaacgga ttgaatggca agagggcgt     1200 agccatggat gcagaaattg ctatcaagag taaagaaaag tatattgaag cttatgaagc    1260
aattactggc aagaaatggg cttgaatgat tagtaccctc ctcgccttt tcagacatct     1320 gaaatttccc ttattcttcc aattccatat aaaatcctat ttaggtaatt agtaaacaat    1380
gatcataaag tgaaatcatt caagtaacca ttccgtttat cgttgattta aaatcaataa    1440
cgaatgaatg tcggtctgag tagtcaattt gttgccttgg agctcattgg caggggtct    1500 tttggctcag                                                          1510

<210> SEQ ID NO 57
<211> LENGTH: 304
```

<212> TYPE: PRT
<213> ORGANISM: Pichia pastoris

<400> SEQUENCE: 57

```
Met Ser Ile Val Asn Thr Asp Leu Asp Gly Ile Leu Pro Leu Ile Ala
 1               5                  10                  15
Lys Gly Lys Val Arg Asp Ile Tyr Ala Val Asp Glu Asn Asn Leu Leu
             20                  25                  30
Phe Val Ala Thr Asp Arg Ile Ser Ala Tyr Asp Val Ile Met Thr Asn
         35                  40                  45
Gly Ile Pro Asp Lys Gly Lys Ile Leu Thr Gln Leu Ser Val Phe Trp
     50                  55                  60
Phe Asp Phe Leu Ala Pro Tyr Ile Lys Asn His Leu Val Ala Ser Asn
 65                  70                  75                  80
Asp Lys Glu Val Phe Ala Leu Leu Pro Ser Leu Ser Glu Glu Lys
                 85                  90                  95
Tyr Lys Ser Gln Leu Glu Gly Arg Ser Leu Ile Val Lys Lys His Arg
            100                 105                 110
Leu Ile Pro Leu Glu Ala Ile Val Arg Gly Tyr Ile Thr Gly Ser Ala
        115                 120                 125
Trp Lys Glu Tyr Lys Asn Ser Lys Thr Val His Gly Val Lys Val Glu
    130                 135                 140
Asn Glu Asn Leu Gln Glu Ser Asp Ala Phe Pro Thr Pro Ile Phe Thr
145                 150                 155                 160
Pro Ser Thr Lys Ala Glu Gln Gly Glu His Asp Glu Asn Ile Ser Ile
                165                 170                 175
Glu Gln Ala Ala Glu Ile Val Gly Lys Asp Ile Cys Glu Lys Val Ala
            180                 185                 190
Val Lys Ala Val Glu Leu Tyr Ser Ala Ala Lys Asn Phe Ala Leu Leu
        195                 200                 205
Lys Gly Ile Ile Ile Ala Asp Thr Lys Phe Glu Phe Gly Leu Asp Glu
    210                 215                 220
Asn Asn Glu Leu Val Leu Val Asp Glu Val Leu Thr Pro Asp Ser Ser
225                 230                 235                 240
Arg Phe Trp Asn Gln Lys Thr Tyr Gln Val Gly Lys Ser Gln Glu Ser
                245                 250                 255
Tyr Asp Lys Gln Phe Leu Arg Asp Trp Leu Thr Ala Asn Gly Leu Asn
            260                 265                 270
Gly Lys Glu Gly Val Ala Met Asp Ala Glu Ile Ala Ile Lys Ser Lys
        275                 280                 285
Glu Lys Tyr Ile Glu Ala Tyr Glu Ala Ile Thr Gly Lys Lys Trp Ala
    290                 295                 300
```

<210> SEQ ID NO 58
<211> LENGTH: 1016
<212> TYPE: DNA
<213> ORGANISM: Artificial Sequence
<220> FEATURE:
<223> OTHER INFORMATION: ADE 2 5' seq for Knockout

<400> SEQUENCE: 58
agttgggccc ttaaaatcat ctgcctcacc ccaccgacca atgggaattc tagaaacaat    60
ttcattgctc ttcttctcgt taccataaga atcggctgtc atgtttgact taacgaaccc   120
tggaacaagg gaattcacgg taatacccttt tggagcaagt tcaaccgata gagccttcat   180
taatgagttg attgcacctt tggtggtcgc atataccgat tgattcgggt aggtcacttc   240

```
gaaactgtac agggaggcag taaagatgat cctaccctta atctggttct taataaagtg      300
tttagtgact agctgtgtca atctaaatgg aaaatcgaca tttacctttt ggatagccgc      360
gtaatctttc tccgtaaaac ttgtaaactc agatttaatg gcaatggcag cgttgttgat      420
taaaatgtca atctttccag tggaactctt ctccaccgca ggactcgtta cggtctcttc      480
cagctttgca agatcggcat ccactagatc caactcaatt gtatgtatgg aggcaccatc      540
ggcatttgac attctcacct cttcaatgaa agccgttggg tctgtagaag gtctatggat      600
aagaataagt tctgcacctg cttcataaag tcctcgaact attccttggc ctaatccgct      660
ggtaccaccg gtgatcaagg cgaccttacc attcaaagaa aacaaatcag cggacattag      720
cgacttgaat agggaatggg ttagacaaat gaaagccgac gagccagcac tttatagtaa      780
gtgcaggtga gtcaataaga ataaatgtat ggcttgctgt ccctatcgcg taagaagctt      840
actaagatcg cctaaattga aaagttgaac aaatcagttc tagctggcct ccatcagcat      900
ttcgttctcc tctgatcatc tttgccaatc gctagcatgc cctcagcgtg caaggaaaag      960
cacgcttctt tcttatcgac gtattttcaa ctatggcaga gccaggttag caagtc       1016
```

<210> SEQ ID NO 59
<211> LENGTH: 1676
<212> TYPE: DNA
<213> ORGANISM: Artificial Sequence
<220> FEATURE:
<223> OTHER INFORMATION: ADE 2 3' seq for Knockout

<400> SEQUENCE: 59

```
atttagtatt gtttttaat agatgtatat ataatagtac acgtaactta tctattccat       60
tcataatttt attttaaagg ttcggtagaa atttgtcctc caaaaagttg gttagagcct      120
ggcagttttg ataggcatta ttatagattg ggtaatattt accctgcacc tggaggaact      180
ttgcaaagag cctcatgtgc tctaaaagga tgtcagaatt ccaacatttc aaaattatat      240
ctgcatgcgt ctgtaatact ggaactgtta tttttctggt caggatttca ccgctcttgt      300
cgtcatgttt ctcgtcgtct gaaagtaaac tgactttcct ctttccataa acacaaaaat      360
cgattgcaac ttggttattc ttgagattga aatttgctgt gtcttcagtg cttagctgaa      420
tatcaacaaa cttacttagt actaataacg aagcactatg gtaagtggca taacatagtg      480
gtattgaagc gaacagtgga tattgaaccc aagcattggc aacatctggc tctgttgata      540
ctgatccgga tcgtttggca ccaattcctg aaacggcgta gtgccaccaa ggtttcgatt      600
tgagaacagg ttcatcatca gagtcaacca ccccaatgtc aatggcaggc tccaacgaag      660
taggtccaac aacaacagga agtatttgac cttgaagatc tgttccttta tgatccacca      720
caccttgccc caattccaat aactttacca gtcccgatgc agacatgata actggtacta      780
atgatctcca ttgattttcg tcggcactac gtaaagcctc caaaaatgaa ttcagaatat      840
cttctgaaac tagattctgc ttctgtgatt caagcattgc tttatgtaga catctcttga      900
ataaaagcaa ttctccacat attggtgtgt gtaagataga tctggaaaga tgtatctgga      960
atagtccagt caacgttgtg caattgatta gcattacctt actgtgaaca tctctatcta     1020
caacaacaga ctcaattcga tagacgttcc gggaaagttt tcaagcgca ttcagtttgc      1080 tgttgaacaa agtgactttg ctttccaatg tgcaaatacc cctgtatatc aagtccatca     1140
catcactcaa gaccttggtg gaaagaatg aaacagctgg agcataattt tcgaatgaat     1200
taggtaaggt cacttcatcc ttatctgttg taatgctata atcaatagcg gaactaacat     1260
```

```
cttcccatgt aacaggtttc ttgatctctg aatctgaatc tttatttgaa aaagaattga   1320
aaaaagactc atcactcatt gggaattcaa ggtcattagg gtattccatt gttagttctg   1380
gtctaggttt aaagggatca ccttcgttaa gacgatggaa aatagctaat ctgtacaata   1440
accagatact tctaacgaag ctctctctat ccatcagttg acgtgttgag gatatctgaa   1500
ctagctcttt ccactgcgaa tcaggcatgc tcgtatagct ggcaagcatg ttattcagct   1560
ttaccaagtt agaagccctt tggaaaccat ctatagattc ccgaaaaaac ttatacccac   1620
tgagggtttc actgagcata gtcagtgaca tcaaagagca tttcaaatcc atctca      1676
```

`<210> SEQ ID NO 60`
`<211> LENGTH: 2018`
`<212> TYPE: DNA`
`<213> ORGANISM: Pichia pastoris`

`<400> SEQUENCE: 60`

```
gtcaaagccg tatactcggt agtgtgctcg ccaaaaataa atttgacttg actcttcact     60
agcctatgca aataaggtta ccttttccaa gaatcgtaga aacgattaaa aaacttccaa    120
actctcatgg attctcaggt aataggtatt ctaggaggag ccagctaggc cgaatgatt    180 gttgaggccg ctagcaggct caatatcaag accgtgattc ttgatgatgg ttttcaccct    240
gctaagcaca ttaatgctgc gcaagaccac atcgacggat cattcaaaga tgaggaggct    300
atcgccaagt tagctgccaa atgtgatgtt ctcactgtag agattgagca tgtcaacaca    360
gatgctctaa agagagttca agacagaact ggaatcaaga tatatccttt accagagaca    420
atcgaactaa tcaaggataa gtacttgcaa aaggaacatt tgatcaagca aacatttcg    480 gtgacaaagt ctcagggtat agaatctaat gaaaaggcgc tgcttttgtt tggagaagag    540
aatggatttc catatctgtt gaagtcccgg actatggctt atgatggaag aggcaatttt    600
gtagtggagt ctaaagagga catcagtaag gcattagaat tcttgaaaga tcgtccattg    660
tatgccgaga gtttgctcc ttttgttaaa gaattagcgg taatggttgt gagatcactg    720
gaaggcgaag tattctccta cccaaccgta gaaactgtgc acaaggacaa tatctgtcat    780
attgtgtatg ctccggccag agttaatgac accatccaaa agaaagctca aatattagct    840
gaaaacactg tgaagacttt cccaggcgct ggaatcttcg gagttgagat gttcctattg    900
tctgatggag aacttcttgt aaatgagatt gctccaaggc cccacaattc tggtcactat    960
acaatcgatg catgtgtaac atctcagttc gaagcacatg taagagccat aactggtctg   1020
ccaatgccac tagatttcac caaactatct acttccaaca ccaacgctat tatgctcaat   1080
gttttgggtg ctgaaaaatc tcacggggaa ttagagtttt gtagaagagc cttagaaaca   1140
cccggtgctt ctgtatatct gtacggaaag accacccgat tggctcgtaa gatgggtcat   1200
atcaacataa taggatcttc catgttggaa gcagaacaaa agttagagta cattctagaa   1260
gaatcaaccc acttaccatc cagtactgta tcagctgaca ctaaaccgtt ggttggagtt   1320
atcatgggtt cagactctga tctacctgtg atttcgaaag gttgcgatat tttaaaacag   1380
tttggtgttc cattcgaagt tactattgtc tctgctcata gaacaccaca gagaatgacc   1440
agatatgcct ttgaagccgc tagtagaggt atcaaggcta tcattgcagg tgctggtggt   1500
gctgctcatc ttccaggaat ggttgctgcc atgactccgt tgccagtcat tggtgttcct   1560
gtcaagggct ctacgttgga tggtgtagac tcgctacact cgattgtcca aatgcctaga   1620
ggtgttcctg tggctacggt tgctatcaac aacgccacca atgccgctct gttggccatc   1680
aggattttag gtacaattga ccacaaatgg caaaaggaaa tgtccaagta tatgaatgca   1740
```

-continued

```
atggagaccg aagtgttggg gaaggcatcc aacttggaat ctgaagggta tgaatcctat    1800
ttgaagaatc gtctttgaat ttagtattgt tttttaatag atgtatatat aatagtacac    1860
gtaacttatc tattccattc ataatttat  tttaaaggtt cggtagaaat ttgtcctcca    1920
aaaagttggt tagagcctgg cagttttgat aggcattatt atagattggg taatatttac    1980
cctgcacctg gaggaacttt gcaaagagcc tcatgtgc                            2018
```

<210> SEQ ID NO 61
<211> LENGTH: 563
<212> TYPE: PRT
<213> ORGANISM: Pichia pastoris

<400> SEQUENCE: 61

Met Asp Ser Gln Val Ile Gly Ile Leu Gly Gly Gln Leu Gly Arg
1               5                   10                  15

Met Ile Val Glu Ala Ala Ser Arg Leu Asn Ile Lys Thr Val Ile Leu
            20                  25                  30

Asp Asp Gly Phe Ser Pro Ala Lys His Ile Asn Ala Ala Gln Asp His
        35                  40                  45

Ile Asp Gly Ser Phe Lys Asp Glu Ala Ile Ala Lys Leu Ala Ala
    50                  55                  60

Lys Cys Asp Val Leu Thr Val Glu Ile Glu His Val Asn Thr Asp Ala
65                  70                  75                  80

Leu Lys Arg Val Gln Asp Arg Thr Gly Ile Lys Ile Tyr Pro Leu Pro
                85                  90                  95

Glu Thr Ile Glu Leu Ile Lys Asp Lys Tyr Leu Gln Lys Glu His Leu
            100                 105                 110

Ile Lys His Asn Ile Ser Val Thr Lys Ser Gln Gly Ile Glu Ser Asn
        115                 120                 125

Glu Lys Ala Leu Leu Leu Phe Gly Glu Glu Asn Gly Phe Pro Tyr Leu
    130                 135                 140

Leu Lys Ser Arg Thr Met Ala Tyr Asp Gly Arg Gly Asn Phe Val Val
145                 150                 155                 160

Glu Ser Lys Glu Asp Ile Ser Lys Ala Leu Glu Phe Leu Lys Asp Arg
                165                 170                 175

Pro Leu Tyr Ala Glu Lys Phe Ala Pro Phe Val Lys Glu Leu Ala Val
            180                 185                 190

Met Val Val Arg Ser Leu Glu Gly Glu Val Phe Ser Tyr Pro Thr Val
        195                 200                 205

Glu Thr Val His Lys Asp Asn Ile Cys His Ile Val Tyr Ala Pro Ala
    210                 215                 220

Arg Val Asn Asp Thr Ile Gln Lys Lys Ala Gln Ile Leu Ala Glu Asn
225                 230                 235                 240

Thr Val Lys Thr Phe Pro Gly Ala Gly Ile Phe Gly Val Glu Met Phe
                245                 250                 255

Leu Leu Ser Asp Gly Glu Leu Leu Val Asn Glu Ile Ala Pro Arg Pro
            260                 265                 270

His Asn Ser Gly His Tyr Thr Ile Asp Ala Cys Val Thr Ser Gln Phe
        275                 280                 285

Glu Ala His Val Arg Ala Ile Thr Gly Leu Pro Met Pro Leu Asp Phe
    290                 295                 300

Thr Lys Leu Ser Thr Ser Asn Thr Asn Ala Ile Met Leu Asn Val Leu
305                 310                 315                 320

Gly Ala Glu Lys Ser His Gly Glu Leu Glu Phe Cys Arg Arg Ala Leu
            325                 330                 335

Glu Thr Pro Gly Ala Ser Val Tyr Leu Tyr Gly Lys Thr Thr Arg Leu
            340                 345                 350

Ala Arg Lys Met Gly His Ile Asn Ile Ile Gly Ser Ser Met Leu Glu
            355                 360                 365

Ala Glu Gln Lys Leu Glu Tyr Ile Leu Glu Glu Ser Thr His Leu Pro
            370                 375                 380

Ser Ser Thr Val Ser Ala Asp Thr Lys Pro Leu Val Gly Val Ile Met
385                 390                 395                 400

Gly Ser Asp Ser Asp Leu Pro Val Ile Ser Lys Gly Cys Asp Ile Leu
                405                 410                 415

Lys Gln Phe Gly Val Pro Phe Glu Val Thr Ile Val Ser Ala His Arg
            420                 425                 430

Thr Pro Gln Arg Met Thr Arg Tyr Ala Phe Glu Ala Ala Ser Arg Gly
            435                 440                 445

Ile Lys Ala Ile Ile Ala Gly Ala Gly Gly Ala Ala His Leu Pro Gly
            450                 455                 460

Met Val Ala Ala Met Thr Pro Leu Pro Val Ile Gly Val Pro Val Lys
465                 470                 475                 480

Gly Ser Thr Leu Asp Gly Val Asp Ser Leu His Ser Ile Val Gln Met
                485                 490                 495

Pro Arg Gly Val Pro Val Ala Thr Val Ala Ile Asn Asn Ala Thr Asn
            500                 505                 510

Ala Ala Leu Leu Ala Ile Arg Ile Leu Gly Thr Ile Asp His Lys Trp
            515                 520                 525

Gln Lys Glu Met Ser Lys Tyr Met Asn Ala Met Glu Thr Glu Val Leu
            530                 535                 540

Gly Lys Ala Ser Asn Leu Glu Ser Glu Gly Tyr Glu Ser Tyr Leu Lys
545                 550                 555                 560

Asn Arg Leu

<210> SEQ ID NO 62
<211> LENGTH: 571
<212> TYPE: PRT
<213> ORGANISM: Saccharomyces cereviseae

<400> SEQUENCE: 62

Met Asp Ser Arg Thr Val Gly Ile Leu Gly Gly Gly Gln Leu Gly Arg
1               5                   10                  15

Met Ile Val Glu Ala Ala Asn Arg Leu Asn Ile Lys Thr Val Ile Leu
            20                  25                  30

Asp Ala Glu Asn Ser Pro Ala Lys Gln Ile Ser Asn Ser Asn Asp His
            35                  40                  45

Val Asn Gly Ser Phe Ser Asn Pro Leu Asp Ile Glu Lys Leu Ala Glu
50                  55                  60

Lys Cys Asp Val Leu Thr Ile Glu Ile Glu His Val Asp Val Pro Thr
65                  70                  75                  80

Leu Lys Asn Leu Gln Val Lys His Pro Lys Leu Lys Ile Tyr Pro Ser
            85                  90                  95

Pro Glu Thr Ile Arg Leu Ile Gln Asp Lys Tyr Ile Gln Lys Glu His
            100                 105                 110

Leu Ile Lys Asn Gly Ile Ala Val Thr Gln Ser Val Pro Val Glu Gln
            115                 120                 125

```
Ala Ser Glu Thr Ser Leu Leu Asn Val Gly Arg Asp Leu Gly Phe Pro
    130                 135                 140

Phe Val Leu Lys Ser Arg Thr Leu Ala Tyr Asp Gly Arg Gly Asn Phe
145                 150                 155                 160

Val Val Lys Asn Lys Glu Met Ile Pro Glu Ala Leu Glu Val Leu Lys
                165                 170                 175

Asp Arg Pro Leu Tyr Ala Glu Lys Trp Ala Pro Phe Thr Lys Glu Leu
            180                 185                 190

Ala Val Met Ile Val Arg Ser Asn Gly Leu Val Phe Ser Tyr Pro
        195                 200                 205

Ile Val Glu Thr Ile His Lys Asp Asn Ile Cys Asp Leu Cys Tyr Ala
    210                 215                 220

Pro Ala Arg Val Pro Asp Ser Val Gln Leu Lys Ala Lys Leu Leu Ala
225                 230                 235                 240

Glu Asn Ala Ile Lys Ser Phe Pro Gly Cys Gly Ile Phe Gly Val Glu
                245                 250                 255

Met Phe Tyr Leu Glu Thr Gly Glu Leu Leu Ile Asn Glu Ile Ala Pro
            260                 265                 270

Arg Pro His Asn Ser Gly His Tyr Thr Ile Asp Ala Cys Val Thr Ser
            275                 280                 285

Gln Phe Glu Ala His Leu Arg Ser Ile Leu Asp Leu Pro Met Pro Lys
    290                 295                 300

Asn Phe Thr Ser Phe Ser Thr Ile Thr Thr Asn Ala Ile Met Leu Asn
305                 310                 315                 320

Val Leu Gly Asp Lys His Thr Lys Asp Lys Glu Leu Glu Thr Cys Glu
                325                 330                 335

Arg Ala Leu Ala Thr Pro Gly Ser Ser Val Tyr Leu Tyr Gly Lys Glu
            340                 345                 350

Ser Arg Pro Asn Arg Lys Val Gly His Ile Asn Ile Ile Ala Ser Ser
    355                 360                 365

Met Ala Glu Cys Glu Gln Arg Leu Asn Tyr Ile Thr Gly Arg Thr Asp
    370                 375                 380

Ile Pro Ile Lys Ile Ser Val Ala Gln Lys Leu Asp Leu Glu Ala Met
385                 390                 395                 400

Val Lys Pro Leu Val Gly Ile Ile Met Gly Ser Asp Ser Asp Leu Pro
                405                 410                 415

Val Met Ser Ala Ala Cys Ala Val Leu Lys Asp Phe Gly Val Pro Phe
            420                 425                 430

Glu Val Thr Ile Val Ser Ala His Arg Thr Pro His Arg Met Ser Ala
    435                 440                 445

Tyr Ala Ile Ser Ala Ser Lys Arg Gly Ile Lys Thr Ile Ile Ala Gly
    450                 455                 460

Ala Gly Gly Ala Ala His Leu Pro Gly Met Val Ala Ala Met Thr Pro
465                 470                 475                 480

Leu Pro Val Ile Gly Val Pro Val Lys Gly Ser Cys Leu Asp Gly Val
                485                 490                 495

Asp Ser Leu His Ser Ile Val Gln Met Pro Arg Gly Val Pro Val Ala
            500                 505                 510

Thr Val Ala Ile Asn Asn Ser Thr Asn Ala Ala Leu Leu Ala Val Arg
    515                 520                 525

Leu Leu Gly Ala Tyr Asp Ser Ser Tyr Thr Thr Lys Met Glu Gln Phe
    530                 535                 540

Leu Leu Lys Gln Glu Glu Glu Val Leu Val Lys Ala Gln Lys Leu Glu
```

```
545                 550                 555                 560
Thr Val Gly Tyr Glu Ala Tyr Leu Glu Asn Lys
                565                 570
```